US010041910B2

(12) United States Patent
Doyle et al.

(10) Patent No.: US 10,041,910 B2
(45) Date of Patent: Aug. 7, 2018

(54) METHOD AND SYSTEM WITH OPPOSITELY-FACING ULTRASONIC TRANSDUCERS FOR DETERMINING TISSUE PATHOLOGY

(75) Inventors: Timothy E. Doyle, Springville, UT (US); Leigh A. Neumayer, Salt Lake City, UT (US)

(73) Assignees: UNIVERSITY OF UTAH RESEARCH FOUNDATION, Salt Lake City, UT (US); UTAH STATE UNIVERSITY, North Logan, UT (US)

( * ) Notice: Subject to any disclaimer, the term of this patent is extended or adjusted under 35 U.S.C. 154(b) by 298 days.

(21) Appl. No.: 13/885,274

(22) PCT Filed: Nov. 14, 2011

(86) PCT No.: PCT/US2011/060514
§ 371 (c)(1),
(2), (4) Date: May 14, 2013

(87) PCT Pub. No.: WO2012/065151
PCT Pub. Date: May 18, 2012

(65) Prior Publication Data
US 2013/0269441 A1    Oct. 17, 2013

Related U.S. Application Data

(60) Provisional application No. 61/413,448, filed on Nov. 14, 2010, provisional application No. 61/473,464, filed on Apr. 8, 2011.

(51) Int. Cl.
G01N 29/07 (2006.01)
G01N 29/11 (2006.01)
G01N 29/46 (2006.01)

(52) U.S. Cl.
CPC ............ *G01N 29/07* (2013.01); *G01N 29/11* (2013.01); *G01N 29/46* (2013.01);
(Continued)

(58) Field of Classification Search
None
See application file for complete search history.

(56) References Cited

U.S. PATENT DOCUMENTS 4,984,567 A * 1/1991 Kageyama et al. .......... 600/438
2005/0148899 A1   7/2005 Walker et al.
(Continued)

FOREIGN PATENT DOCUMENTS

WO    96/15446    5/1996
WO   2012/065151   5/2012

OTHER PUBLICATIONS

Scheipers ("Ultrasonic Multifeature Tissue Characterization for Prostate Diagnostics," Ultrasound in medicine & biology, vol. 29, p. 1137-1149, 2003.*
(Continued)

*Primary Examiner* — G. Steven Vanni
(74) *Attorney, Agent, or Firm* — Michael Best & Friedich LLP

(57) ABSTRACT

A method for determining a pathology of a tissue sample. The method includes steps of coupling the tissue sample between two oppositely-facing ultrasonic transducers; acquiring a pulse-echo ultrasonic measurement and a through-transmission ultrasonic measurement of the tissue sample using the ultrasonic transducers; analyzing at least one of the pulse-echo ultrasonic measurement and the through-transmission ultrasonic measurement using time domain analysis; analyzing at least one of the through-transmission ultrasonic measurements and the pulse-echo ultrasonic measurements using frequency domain analysis;
(Continued)

and determining the pathology of the tissue sample based on at least one of the time domain analysis and the frequency domain analysis.

13 Claims, 23 Drawing Sheets

(52) U.S. Cl.
CPC .............. *G01N 2291/02475* (2013.01); *G01N 2291/02854* (2013.01); *G01N 2291/102* (2013.01)

(56) References Cited

U.S. PATENT DOCUMENTS

2006/0130587 A1* 6/2006 Howard ................. G01N 29/07
73/606
2007/0167778 A1 7/2007 Crowley

OTHER PUBLICATIONS

Holmes ("Ultrasonic Imaging of Biofilms Utilizing Echoes from the Biofilm/Air Interface," IEEE Transactions on Ultrasonics, Ferroelectrics, and Frequency Control, vol. 53, p. 185-192, 2006.*

Anscher MS, et al., "Local failure and margin status in early-stage breast carcinoma treated with conservation surgery and radiation therapy." Annals ofSurgery 1993, 218:22-28.

Baddour RE, et al., "High-frequency ultrasound scattering from microspheres and single cells." J. Acoust. Soc. Am. 2005, 117:934-943.

Banihashemi R, et al., "Ultrasound imaging of apoptosis in tumor response: Novel preclinical monitoring of photodynamic therapy effects." Cancer Res. 2008, 68:8590-8596.

Bige Y, et al., "Analysis of microstructural alterations of normal and pathological breast tissue in vivo using the AR cepstrum." Ultrasonics 2006, 44:211-215.

Brand S, et al., "Monitoring of cell death in epithelial cells using high frequency ultrasound spectroscopy." Ultrasound Med. Biol. 2009, 35:482-493.

Bruno I, et al., "Ex vivo breast tissue imaging and characterization using acoustic microscopy." In Acoustical Imaging. vol. 28. Edited by Andre MP. Dordrecht: Springer; 2007:279-287.

Cabioglu N, et al., "Role for intraoperative margin assessment in patients undergoing breast-conserving surgery." Ann. Surg. Oncol. 2007, 14:1458-1471.

Cendan JCD, et al., "Accuracy of intraoperative frozensection analysis of breast cancer lumpectomy—bed margins." J. Am. Coll. Surg. 2005, 201:194-198.

Czamota GJ, et al., "Ultrasound imaging of apoptosis: high-resolution noninvasive monitoring of programmed cell death in vitro, in situ, and in vivo." Br. J Cancer 1999, 81:520-527.

Daoud MI, et al., "Stochastic modeling of normal and tumor tissue microstructure for high-frequency ultrasound imaging simulations." IEEE Trans. Biomed. Eng. 2009, 56:2806-2815.

Dick AW, et al., "Comparative effectiveness of ductal carcinoma in situ management and the roles of margins and surgeons." J Natl. Cancer Inst. 2011, 103:92-104.

Doyle TE, et al., "High-frequency ultrasound for intraoperative margin assessments in breast conservation surgery: a feasibility study." BMC Cancer 2011, 11:444.

Doyle TE, et al., "Histology-based simulations for the ultrasonic detection of microscopic cancer in vivo." J Acoust. Soc. Am. 2007, 122:EL210-EL216.

Doyle TE, et al., "Simulation of elastic wave scattering in cells and tissues at the microscopic cancer level." J. Acoust. Soc. Am. 2009, 125:1751-1767.

Doyle TE, et al., "Ultrasonic differentiation of normal versus malignant breast epithelial cells in monolayer cultures." J. Acoust. Soc. Am. 2010, 128:EL229-EL235.

Fitzgerald AJ, et al., "Terahertz pulsed imaging of human breast tumors." Radiology 2006, 239:533-540.

Gemmeke H, et al., "3D ultrasound computer tomography for medical imaging. Nuclear Instruments and Methods in Physics Research Section A: Accelerators, Spectrometers, Detectors and Associated Equipment 2007," 580(2): 1057-1065.

Haka AS, et al., "Diagnosing breast cancer using Raman spectroscopy: prospective analysis." J. Biomed. Opt. 2009, 14:054023.

Haka AS, et al., "In vivo margin assessment during partial mastectomy breast surgery using Raman spectroscopy." Cancer Res. 2006, 66:3317-3322.

Henni AH, et al., "Three-dimensional transient and harmonic shear-wave scattering by a soft cylinder for dynamic vascular elastography." J. Acoust. Soc. Am. 2008, 124:2394-2405.

Huang SW, et al., "Ultrasonic computed tomography reconstruction of the attenuation coefficient using a linear array." IEEE Trans. Ultrason. Ferroelectr. Freq. Control 2005, 52:2011-2022.

Hunt JW, et al., "A model based upon pseudo regular spacing of cells combined with the randomization of the nuclei can explain the significant changes in highfrequency ultrasound signals during apoptosis." Ultrasound Med. Biol. 2002, 28, 217-226.

Insana MF, "Modeling acoustic backscatter from kidney microstructure using an anisotropic correlation function." J. Acoust. Soc. Am. 1995, 97:649-655.

Jeong JW, et al., "Differentiation of cancerous lesions in excised human breast specimens using multiband attenuation profiles from ultrasonic transmission tomography." J. Ultrasound Med. 2008, 27:435-451.

Keller MD, et al., "Autofluorescence and diffuse reflectance spectroscopy and spectral imaging for breast surgical margin analysis." Lasers Surg. Med. 2010, 42:15-23.

Kennedy S, et al., "Optical breast cancer margin assessment: an observational study of the effects of tissue heterogeneity on optical contrast." Breast Cancer Research 2010, 12:R91.

Klimberg VS, et al., "Use of touch preps for diagnosis and evaluations of surgical margins in breast cancer." Ann. Surg. Oncol. 1998, 5:220-226.

Lanfranchi ME, "Breast Ultrasound." 2nd edition. New York: Marban Books; 2000.

Li C, et al., "Breast imaging using transmission ultrasound: reconstructing tissue parameters of sound speed and attenuation." In 2008 International Conference on BioAfedical Engineering and Informatics: 27-30 Afay 2008; Sanya, China. Edited by Peng Y, Zhang Y. Piscataway: IEEE; 2008:708-712.

Lizzi FL, et al., "Statistical framework for ultrasonic spectral parameter imaging." Ultrasound Med. Biol. 1997, 23:1371-1382.

Lizzi FL, et al., "Theoretical framework for spectrum analysis in ultrasonic tissue characterization." J. Acoust. Soc. Am. 1983, 73:1366-1373.

Mamou J, et al., "Extended threedimensional impedance map methods for identifying ultrasonic scattering sites." J Acoust. Soc. Am. 2008, 123:1195-1208.

Mamou J, et al., "Singular spectrum analysis applied to ultrasonic detection and imaging of brachytherapy seeds." J Acoust. Soc. Am. 2007, 121:1790-1801.

Moore MM, et al., "Association of infiltrating lobular carcinoma with positive surgical margins after breast-conservation therapy." Annals of Surgery 2000, 231:877-882.

Moore MM, et al., "Intraoperative ultrasound is associated with clear lumpectomy margins for palpable infiltrating ductal breast cancer." Annals of Surgery 2001, 233:761-768.

Nguyen F, et al., "Intraoperative evaluation of breast tumor margins with optical coherence tomography." Cancer Res. 2009, 69:8790-8796.

Oelze ML, et al., "Application of three scattering models to characterization of solid tumors in mice." Ultrason. Imaging 2006, 28:83-96.

Oelze ML, et al., "Characterization of tissue microstructure using ultrasonic backscatter: Theory and technique for optimization using a Gaussian form factor." J. Acoust. Soc. Am. 2002, 112:1202-1211.

Oelze ML, et al., "Examination of cancer in mouse models using highfrequency quantitative ultrasound." Ultrasound Med. Biol. 2006, 32:1639-1648.

(56) References Cited

OTHER PUBLICATIONS

Oelze ML, et al., "Quantitative ultrasound assessment of breast cancer using a multiparameter approach." In 2007 IEEE Ultrasonics Symposium: Oct. 28-31, 2007; New York. Edited by Yuhas MP. Piscataway: IEEE; 2007:981-984.
Olsha O, et al., "Resection margins in ultrasound-guided breast-consening surgery." Ann. Surg. Oncol. 2011, 18:447-452.
Olson TP, et al., "Frozen section analysis for intraoperative margin assessment during breast-conserving surgery results in low rates of re-excision and local recurrence." Ann. Surg. Oncol. 2007, 14:2953-2960.
Pappo I, et al., "Diagnostic performance of a novel device for real-time margin assessment in lumpectomy specimens." J. Surg. Res. 2010, 160:277-281.
Rose JH, et al., "A proposed microscopic elastic wave theory for ultrasonic backscatter from myocardial tissue." J. Acoust. Soc. Am. 1995, 97:656-668.
Roukos DH, et al., "Perspectives and risks of breastconservation therapy for breast cancer." Ann. Surg. Oneal. 2003, 10:718-721.
Sakr RA, et al., "Clear margins for invasive lobular carcinoma: a surgical challenge." Eur. J. Surg. Oncol. 2011, 37:350-356.
Sanpanich et al., "3D Ultrasound Reflection Tomography With Matrix Linear Array Transducer," The 3rd International Symposium on Biomedical Engineering (ISBME 2008) pp. 351-355.
Savery D, et al., "High-frequency ultrasound backscattering by blood: Analytical and semianalytical models of the erythrocyte cross section." J Acoust. Soc. Am. 2007, 121:3963-3971.
Shimauchi A, et al., "Comparison of MDCT and MRI for evaluating the intraductal component of breast cancer." Amer. J. Roentgenology 2006, 187:322-329.
Stotzka R, et al., "A New 3D Ultrasound Computer Tomography Demonstration System." European Congress on Radiology 2004 (2 pages).
Taggart LR, et al., "Ultrasonic characterization of whole cells and isolated nuclei." Ultrasound Med. Biol. 2007, 33:389-401.
Valdes EK, et al., "Intra-operative touch preparation cytology; does it have a role in re-excision lumpectomy?" Ann. Surg. Oncol. 2007, 14:1045-1050.
Vlad RM, et al., "Evaluating the extent of cell death in 3D high frequency ultrasound by registration with whole-mount tumor histopathology." Afed. Phys. 2010, 37:4288-4297.
Wear KA, "Autocorrelation and cepstral methods for measurement of tibial cortical thickness." IEEE Trans. Ultrason. Ferroelectr. Freq. Control 2003, 50:655-660.
Wear KA, et al., "Application of autoregressive spectral analysis to cepstral estimation of mean scatterer spacing." IEEE Trans. Ultrason. Ferroelectr. Freq. Control 1993, 40:50-58.
PCT/US2011/060514 International Search Report and Written Opinion dated Feb. 27, 2012 (7 pages).

\* cited by examiner

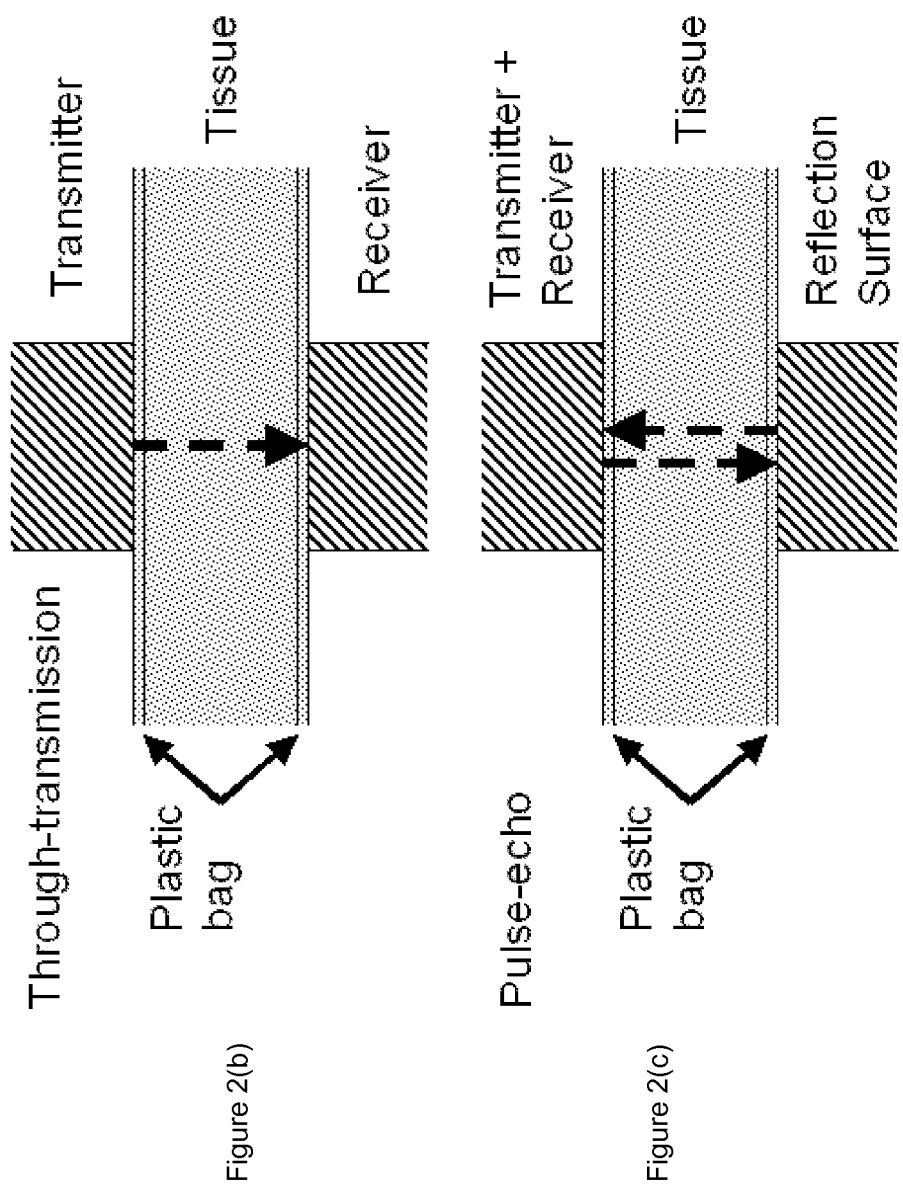

METHOD AND SYSTEM WITH OPPOSITELY-FACING ULTRASONIC TRANSDUCERS FOR DETERMINING TISSUE PATHOLOGY

RELATED APPLICATIONS

This application is a national stage filing under 35 U.S.C. 371 of International Application No. PCT/US2011/060514 filed Nov. 14, 2011, which claims the benefit under 35 U.S.C. § 119(e) of U.S. Provisional Patent Application No. 61/413,448, filed Nov. 14, 2010, titled "ULTRASONIC METHOD FOR DETERMINING TISSUE PATHOLOGY" and of U.S. Provisional Patent Application No. 61/473,464, filed Apr. 8, 2011, titled "ULTRASONIC METHOD FOR DETERMINING TISSUE PATHOLOGY," each of which is incorporated herein by reference.

GOVERNMENT SUPPORT

This invention was made with government support under R21 CA131798 awarded by the National Institutes of Health. The Government has certain rights in the invention.

FIELD OF THE INVENTION

The present disclosure relates to an ultrasonic method to determine the pathology of tissues during or immediately following surgery.

BACKGROUND

Breast cancer impacts 12.2% of women in the United States, with a third of all patients dying from the disease. Approximately half of breast cancer patients elect to have breast conservation surgery (BCS), also known as lumpectomy, as an alternative to mastectomy as a major part of their treatment. A recent study of 994 women diagnosed with ductal carcinoma in situ (DCIS) showed that both treatment strategy (BCS alone, BCS with radiation therapy, or mastectomy) and margin status strongly correlated with long-term ipsilateral disease-free survival, but that positive or close margins following the last surgical treatment significantly reduced 5-year and 10-year ipsilateral event-free survival independent of treatment strategy.

Several approaches are therefore being investigated for the pre-operative and intraoperative estimation of margin sizes as well as for the intraoperative detection of cancer in surgical margins. Methods studied for the estimation of margin sizes include pre-operative CT and MRI and intraoperative ultrasonic imaging with conventional medical ultrasound instrumentation. A number of electromagnetic and optical methods are also being developed for the intraoperative detection of cancer in margins. These include terahertz imaging, Raman spectroscopy, optical coherence tomography, and diffuse reflectance spectroscopy. Intraoperative pathology methods currently being used for margin assessments include touch preparation cytology and frozen section analyses. These methods have limitations, however, including the requirement for an on-site trained pathologist, the inability to identify close margins (touch preparation cytology), and the ability to sample only a small portion of the margin (frozen section analyses).

Since removal of all of the cancer in BCS, and in other cancer surgeries, is critical to preventing local recurrence of the malignancy, surgeons strive to obtain negative margins (cancer free tissues surrounding the tumor). Using current techniques, however, a surgeon cannot determine the pathology of the margins in the operating room, and conventional pathology takes 2-4 days to analyze the specimens. Currently, 30-50% of BCS patients require re-excision due to positive margins, resulting in additional patient suffering and health care costs. Therefore, surgeons urgently need a real-time technique to determine the pathology of surgical margins during cancer surgery.

SUMMARY

In one embodiment the invention provides a method for determining a pathology of a tissue sample. The method includes steps of coupling the tissue sample between two oppositely-facing ultrasonic transducers; acquiring a pulse-echo ultrasonic measurement and a through-transmission ultrasonic measurement of the tissue sample using the ultrasonic transducers; analyzing at least one of the pulse-echo ultrasonic measurement and the through-transmission ultrasonic measurement using time domain analysis; analyzing at least one of the through-transmission ultrasonic measurements and the pulse-echo ultrasonic measurements using frequency domain analysis; and determining the pathology of the tissue sample based on at least one of the time domain analysis and the frequency domain analysis.

In another embodiment, the invention provides a system for determining a pathology of a tissue sample. The system includes a pair of oppositely-facing ultrasonic transducers coupled to the tissue sample and a controller operatively coupled to the transducers. The controller is configured to acquire a pulse-echo ultrasonic measurement and a through-transmission ultrasonic measurement of the tissue sample using the ultrasonic transducers; analyze at least one of the pulse-echo ultrasonic measurement and the through-transmission ultrasonic measurement using time domain analysis; analyze at least one of the through-transmission ultrasonic measurements and the pulse-echo ultrasonic measurements using frequency domain analysis; and determine the pathology of the tissue sample based on at least one of the time domain analysis and the frequency domain analysis.

Other aspects of the invention will become apparent by consideration of the detailed description and accompanying drawings.

BRIEF DESCRIPTION OF THE DRAWINGS

FIG. 2(b) shows a diagram of the through-transmission mode.

FIG. 2(c) shows a diagram of the pulse-echo mode.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Many studies have shown that ultrasonic wave propagation in tissues is strongly dependent on histological features including cell structure, cell number density, tissue microstructure, and tissue heterogeneity. Ultrasound therefore presents the potential of being able to differentiate between normal, benign, and malignant pathologies in breast tissue. Of specific relevance to margin assessments was a study performed on eight mastectomy specimens using ultrasound transmission tomography from 2-10 MHz. The frequency dependent attenuation was used to classify regions of each specimen into three types of tissue: Normal, benign changes, and invasive carcinoma. The high spatial resolution of the scans (≤1 mm) permitted a high degree of correlation to pathology micrographs, and yielded an 80% sensitivity, 90% specificity, and 86% accuracy for the three-way classification method.

High-frequency (HF) ultrasound has also been shown to be sensitive to changes in cell and tissue histology associated with mouse mammary tumors, apoptosis of malignant cells in centrifuged and dilute cell suspensions in vitro, apoptosis of malignant cells in rat tissues ex vivo and in vivo, and apoptosis in mouse tumors following photodynamic and radiation therapies. Normal and malignant human breast epithelial cells have additionally been differentiated in vitro in monolayer cell cultures using 20-50 MHz ultrasound, and tumor size and margin status in 2-5 mm thick ductal carcinoma specimens have been determined with 15-50 MHz scanning acoustic microscopy.

In addition to experimental measurements, numerical models of ultrasonic wave propagation at the microstructural level have shown that HF ultrasound may be sensitive to tissue pathology. Experimental studies using normal and malignant monolayer cultures of human breast epithelial cells as well as mouse liver specimens have validated the modeling approaches.

This study was performed to determine if HF ultrasound (20-80 MHz) could provide pathology sensitive measurements for the ex vivo detection of cancer in surgical margins obtained during breast conservation surgery. Both pulse-echo and through-transmission measurements were performed on the breast tissue specimens. The data analysis included examining conventional ultrasonic parameters such as ultrasonic sound speed and attenuation for correlations to pathology, as well as developing new approaches to analyze ultrasonic spectra and cepstra.

Figure 1A:
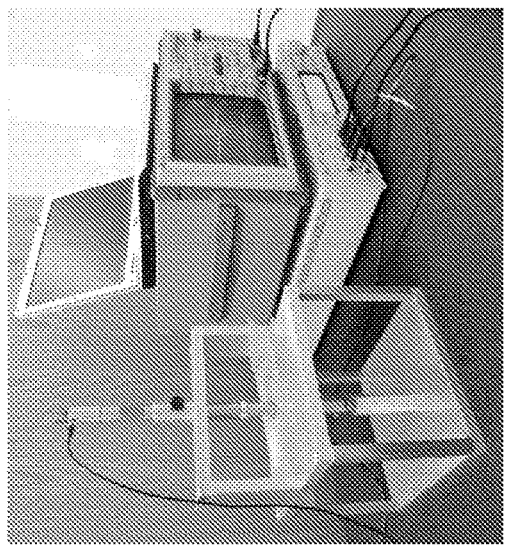
FIG. 1(a) shows a photograph of an aluminum test fixture with instrumentation.

Accordingly, a high-frequency (HF) ultrasonic test system (FIG. 1(a)) has been developed to collect simultaneous pulse-echo and through-transmission measurements from margins and other tissue specimens following resection from BCS. The data have been analyzed with a variety of methods to search for correlations to tissue pathology.

The invention includes ultrasonic-based methods and systems for determining tissue pathology. In various embodiments, the methods and systems include acquiring pulse-echo and through-transmission ultrasonic waveforms from tissue samples using a high-frequency (approximately 10-100 MHz) ultrasonic pulser-receiver and broadband, high-frequency ultrasonic transducers or transducer arrays.

During the measurement procedure, the tissue sample is placed in, for example, a sterile plastic bag. The bag is placed between two oppositely facing, coaxially aligned transducers and coupled to the transducers with ultrasonic gel. Both pulse-echo and through-transmission waveforms are then collected from the tissue sample by pulsing the transducer with a spike pulse or square-wave pulse at the transducer's peak frequency (e.g. 50 MHz) and collecting either the first waveform reflected from the receiving transducer's face (pulse-echo mode) or from the first waveform transmitted through the specimen (through-transmission mode). The time-domain waveforms are then converted to ultrasonic spectra and cepstra using a Fourier transform (e.g. a fast Fourier transform (FFT)) along with other signal processing algorithms. The waveforms, spectra, and cepstra are then analyzed to determine the tissue pathology.

In various embodiments, data analysis is performed by obtaining variables from the waveforms, spectra, and cepstra that are sensitive to tissue pathology. These include ultrasonic sound speed and attenuation from the waveforms, the number of peaks in a certain range of the spectrum (peak density), or the slopes of the cepstra or portions thereof. These variables are correlated to tissue pathology using conventional pathology results obtained from optical microscopy as well as computer simulations of ultrasonic scattering in said tissues. A multivariate analysis of the variables is performed to improve the sensitivity, selectivity, and accuracy of the approach.

In one particular embodiment, the methods and systems of the invention are used for the detection of microscopic cancer in the surgical margins of patients undergoing breast conservation surgery (lumpectomy) or other oncological surgeries. The margins are a layer of tissue surrounding the tumor that the surgeon removes in order to ensure the cancer has been fully excised. The presence of cancer in surgical margins (i.e., positive margins) requires that the patient return for a second surgery to remove more tissue to obtain negative margins.

In other embodiments, the methods and systems of the invention may be applied to improve clinical practice for other soft tissue procedures such as endoscopy, biopsy, and surgery. For example, in Mohs surgery for skin cancer—where successive layers of skin tissue are removed in stages and examined for remaining cancer—the ability to determine margin status rapidly, accurately, and with high resolution would lead to less operating time, fewer surgical complications, and improved patient outcome. Although HF ultrasound has been studied for use in Mohs surgery, only traditional imaging methods were investigated in comparison to the spectral analysis and molecular pathology methods proposed herein. Such an approach would be useful in surgeries involving cancers that have been molecularly subtyped such as melanoma. Still other potential applications of this technology include instant biopsies, margin evaluations for other soft-tissue cancers such as colorectal cancer, liver cancer, prostate cancer, and pancreatic cancer, as well as non-oncology applications such as diagnosis of tissue necrosis and inflammation.

Immediately following resection, the surgeon places each specimen inside a resealable plastic storage bag for ultrasonic testing, and labeled the bag with an identified specimen number and, if applicable, the orientation of the margin. During ultrasonic testing, the outside of the bag is coupled to the ultrasonic transducers with ultrasound scanning gel (e.g. Sonotech Clear Image). In general, the surface moisture of the tissue provides sufficient coupling of the specimen to the inside of the bag for ultrasonic transmission. The bag prevents contamination of the specimen with coupling fluid and additionally provides improved transmission of ultrasound between the transducers and specimen. One to four sites were tested on each specimen depending on the specimen size, resulting in a total of 57 sites tested. Triplicate waveforms were acquired from each test site on a specimen. After ultrasonic testing, routine pathology analyses were performed on the specimens. Ultrasonic results were correlated to pathology reports for each specimen.

Ultrasonic tests were performed on resected margins and other tissues obtained from 17 patients, resulting in 34 specimens that were classified into 15 pathology categories. Pulse-echo and through-transmission measurements were acquired from a total of 57 sites on the specimens using two single-element 50-MHz transducers. Ultrasonic attenuation and sound speed were obtained from time-domain waveforms. The waveforms were further processed with fast Fourier transforms to provide ultrasonic spectra and cepstra. The ultrasonic measurements and pathology types were analyzed for correlations. The specimens were additionally re-classified into five pathology types to determine specificity and sensitivity values.

In general, the density of peaks in the ultrasonic spectra, a measure of spectral structure, showed significantly higher values for carcinomas and precancerous pathologies such as atypical ductal hyperplasia than for normal tissue. The differences in peak density correlated to numerical models of neoplastic changes in both mammary ducts and in random, uniform distributions of cells. The slopes of the cepstra for non-malignant pathologies displayed significantly greater values that differentiated them from the normal and malignant tissues. The attenuation coefficients were sensitive to fat necrosis, fibroadenoma, and invasive lobular carcinoma. Specificities and sensitivities for differentiating pathologies from normal tissue were 100% and 86% for lobular carcinomas, 100% and 74% for ductal carcinomas, 80% and 82% for benign pathologies, and 80% and 100% for fat necrosis and adenomas. Specificities and sensitivities were also determined for differentiating each pathology type from the other four using a multivariate analysis. The results yielded specificities and sensitivities of 85% and 86% for lobular carcinomas, 85% and 74% for ductal carcinomas, 100% and 61% for benign pathologies, 84% and 100% for fat necrosis and adenomas, and 98% and 80% for normal tissue.

The data were analyzed with a variety of methods to search for correlations to tissue pathology. Complementary numerical models using multipole expansion methods were additionally developed to simulate the ductal structure of breast tissue and ultrasonic wave propagation through ducts with normal, benign, and malignant pathologies. Simulation results were compared to the experimental data and pathology results for verification of correlations.

Clinical Protocol

Figure 1B:
FIG. 1(b) shows a tissue sample in a re-sealable plastic bag.

The ultrasonic testing of tissue specimens obtained during the course of routine breast conservation surgery was approved by the University of Utah Institutional Review Board on Oct. 14, 2009, as a minimal risk study (IRB #00037350). Informed consent was obtained from patients for the use of their tissues for research purposes. Surgeries were performed on 17 patients at the Huntsman Cancer Hospital, Salt Lake City, Utah. The surgeries provided 34 resected specimens consisting of margins and other tissues such as lymph nodes and adenomas. The samples ranged from 1-5 cm in length and width, 0.1-1.5 cm in thickness, comprised a spectrum of both benign and malignant tissue pathologies, and did not require any additional procedures or resection that affected the patient or surgical outcome. Table 1 lists the range of pathologies provided by the specimens. For the purposes of this study the pathologies were categorized into 15 classifications. Immediately following resection, the surgeon placed each specimen inside a re-sealable plastic storage bag for ultrasonic testing (FIG. 1 (b)), and labeled the bag with a de-identified specimen number and, if applicable, the orientation of the margin.

TABLE 1

Pathology, number of specimens, and number of positions tested with high-frequency ultrasound. Acronyms in parentheses are used in subsequent figures.

| Tissue type | Specimens | No. of test positions |
|---|---|---|
| Lymph nodes (LN) | 3 | 2 |
| Benign or normal breast (BB) | 4 | 5 |
| Benign breast with calcifications (BC) | 2 | 3 |
| Atypical ductal hyperplasia (ADH) | 2 | 5 |
| Fibrocystic change (FC) | 2 | 6 |
| Fat necrosis (FN) | 1 | 1 |
| Fibroadenoma (FA) | 2 | 2 |
| Tubular adenoma (TA) | 1 | 1 |
| Papilloma (PA) | 4 | 4 |
| Total benign | 21 | 29 |
| Ductal carcinoma in situ (DCIS) | 3 | 6 |
| DCIS, solid and cribriform (DCIS-SC) | 2 | 3 |
| DCIS + IDC | 3 | 9 |
| Invasive ductal carcinoma (IDC) | 2 | 3 |
| Lobular carcinoma in situ (LCIS) | 2 | 4 |
| Invasive lobular carcinoma (ILC) | 1 | 3 |
| Total Malignant | 13 | 28 |

During ultrasonic testing, the outside of the bag was coupled to the ultrasonic transducers with ultrasound scanning gel (Sonotech® Clear Image). The surface moisture of the tissue provided sufficient coupling of the specimen to the inside of the bag for ultrasonic transmission. The bag therefore prevented contamination of the specimen with coupling fluid and additionally provided improved transmission of ultrasound between the transducers and specimen. One to four sites were tested on each specimen depending on the specimen size, resulting in a total of 57 sites tested. Triplicate waveforms were acquired from each test site on a specimen. After ultrasonic testing, routine pathology analyses were performed on the specimens. Ultrasonic results were correlated to pathology reports for each specimen.

Ultrasonic Materials and Procedure

Figure 2A:
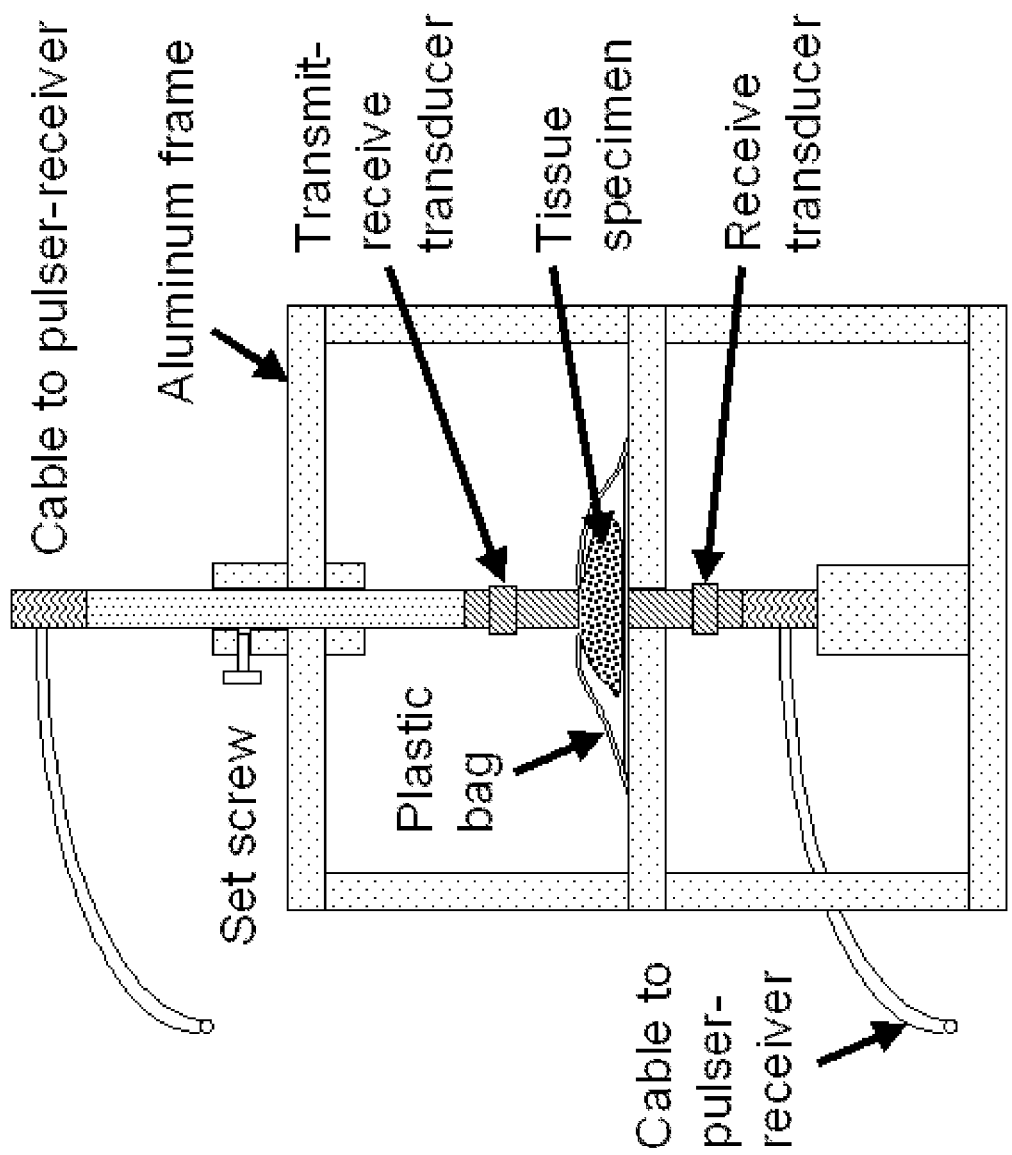
FIG. 2(a) shows a diagram of an aluminum test fixture.

In some embodiments, ultrasonic pulse-echo and through-transmission data were acquired from breast tissue specimens with the use of two immersion transducers (Olympus NDT, V358-SU, 50 MHz, 0.635-cm diameter active element), a HF square-wave pulser/receiver (UTEX, UT340), and a digital storage oscilloscope (Hewlett-Packard, HP-54522A, 500 MHz, 1 Gs/s). Ultrasonic waveforms were averaged in the signal acquisition and downloaded onto a notebook PC using LabVIEW. The data acquisition parameters were pulse voltage=100 V, pulse width=10 ns, pulse repetition rate=5 kHz, and receiver gain=0-48 dB. An aluminum test fixture, FIG. 2(a), was used to support the tissue sample, to position the transducers both above and below the sample for simultaneous pulse-echo and through-transmission measurements, and to lock the transducers into position. The thickness of the specimen was recorded for each ultrasonic measurement. A description was also recorded for each specimen, and photographs were taken of 19 specimens (e.g., FIG. 1(b)).

Figure 1C:
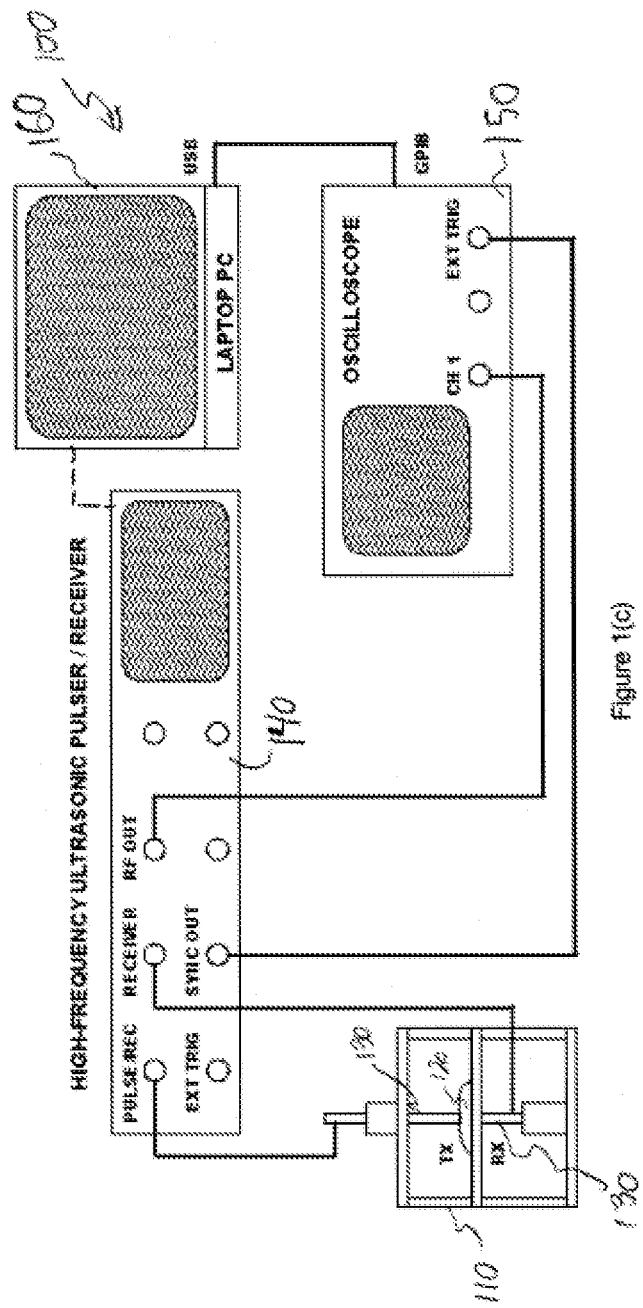
FIG. 1(c) shows a diagram of a system for ultrasonic data collection.

FIG. 1(c) shows a diagram of a system 100 according to embodiments of the invention. The system 100 includes a test fixture 110, which supports the tissue sample 120 as well as the ultrasonic transducers 130. The system 100 also includes a HF ultrasonic pulser/receiver 140, a digital storage oscilloscope 150, and a computer 160. The pulser/receiver is operatively coupled to the ultrasonic transducers 130 as well as to the oscilloscope 150, which in turn is operatively coupled to the computer 160. In some embodiments, the computer 160 is also operatively coupled to the pulser/receiver 140, e.g. in order to send commands to the pulser/receiver 140 to collect data. By 'operatively coupled' is meant any type of wired or wireless connection between the listed components. In other embodiments, the functions of the pulser/receiver 140, the oscilloscope 150, and/or the computer 160 are carried out by a single component, which may be custom-designed to carry out multiple functions in a single unit.

In various embodiments, the computer 160 is connected in a wired or wireless manner to other computers and/or to a larger network such as the Internet. The computer 160 may act as a controller to carry out the functions of the systems or steps of the methods of the invention. The computer includes a microprocessor, memory, data storage, networking and communications, input (e.g. mouse, keyboard, touch screen, touchpad, microphone, camera, etc.), and output (e.g. monitor or other display, speaker, tactile device, printer, etc.) capabilities. In certain embodiments, the microprocessor is programmed to carry out the methods and to control the systems of the invention. The invention also includes computer-readable media (e.g. electronic, magnetic, or other forms of computer-readable storage and memory) containing software with instructions for carrying out the invention.

In some embodiments, the HF ultrasonic test system is made more portable by replacing the digital oscilloscope with a new, more easily transportable oscilloscope having greater capabilities (e.g. Agilent DSO9064A, 600 MHz, 4-channel). In other embodiments, data processing software is written in LabVIEW or Matlab to analyze the ultrasonic signals in real time for parameters that are found to be sensitive to pathology, including attenuation, spectral peak density, and cepstral slope.

The ultrasonic transducers each have a center frequency of 50 MHz and are broadband transducers (providing a range of 20-80 MHz), providing a short pulse length and enhanced signal-to-noise in highly scattering or attenuating materials. The broadband characteristics of the transducers are desirable for obtaining an ultrasonic tissue response across a wide frequency band.

In some embodiments the ultrasonic transducers comprise a pair of high-frequency (HF) ultrasonic linear arrays (e.g. VisualSonics MicroScan™ transducers, MS700, 30-70 MHz). The one-dimensional (1D) linear arrays are used in some embodiments in place of single-element transducers to provide both through-transmission and pulse-echo line scans across and through the interrogated tissue (FIGS. 13(a) and 13(b)). In one embodiment, the arrays are linked to the HF pulser-receiver using a high-voltage radio-frequency switch system (e.g. a design based on Model #50S-1256 by JFW Industries). The switch system permits the operation of individual array element pairs by the data acquisition computer to construct a linear map of the tissue (FIG. 13(a)). In addition to linear arrays, other types of 1D arrays that may be used include curved sector-type arrays.

In various embodiments, the HF ultrasonic arrays include two-dimensional (2D) arrays of transducers that can be operated simultaneously or individually. These arrays may include square, triangular, or hexagonal matrix arrays in addition to segmented annular arrays. In other embodiments, the HF ultrasonic arrays include a single line of transducers that are mechanically scanned relative to the sample.

In one embodiment, the system can be used to operate alternate pairs of elements to generate a data set for tomographic reconstruction of the interior of the tissue (FIG. 13(b)) (methods for collection and tomographic reconstruction of samples from ultrasonic data are known to those skilled in art, e.g. see Stotzka et al., Gemmeke et al., and Sanpanich et al., below). In certain embodiments, data is collected from one or more individual elements of the array. In various embodiments, the data collected by one or more transducers is subjected to the analyses disclosed herein, whether the data is obtained from a column, z-axis slice, 'voxel' (volumetric picture element) or other portion of the sample.

Figure 13:
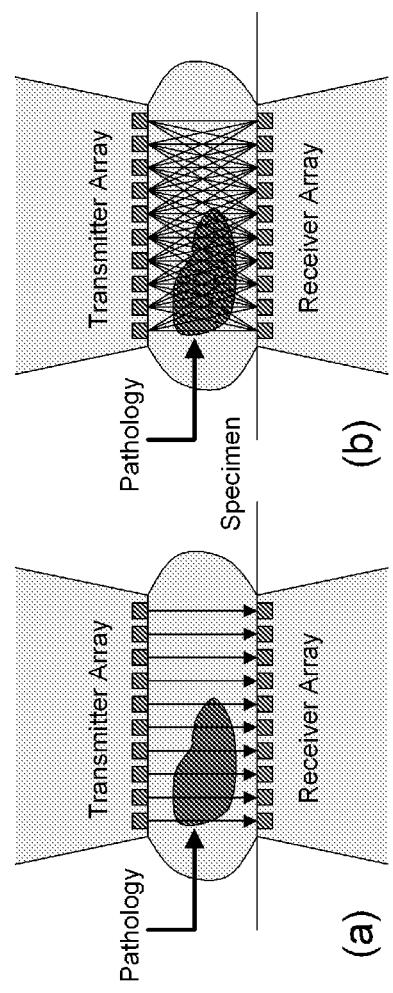
FIG. 13(a) shows one mode of operation of the ultrasonic array, namely linear pulse-echo or through-transmission mode.
FIG. 13(b) shows another mode of operation of the ultrasonic array, namely tomographic through-transmission mode.

Conventional ultrasonic imaging systems would likely be less suitable for the embodiments shown in FIGS. 13(a) and 13(b) because: (1) the tissue sample is imaged in through-transmission mode rather than only a phased-array or B-scan mode, and (2) conventional ultrasonic imaging systems do not have the capability to collect the spectral information that is used for extracting the parameters that correlate to tissue pathology, as disclosed herein.

In various embodiments, the two-dimensional square array, which includes separate transmitter and receiver arrays, operates in a sequential mode. Each element in the transmitter array transmits independently from the others. The signals propagate through the tissue and are received by one or more elements in the receiver array. This mode of operation is in contrast to a phased array, where focusing the ultrasonic beam in the tissue through an electronic approach that pulses the array elements in concert to create constructive and destructive interference of wave fields.

Ultrasonic Data Analysis

Figure 14:
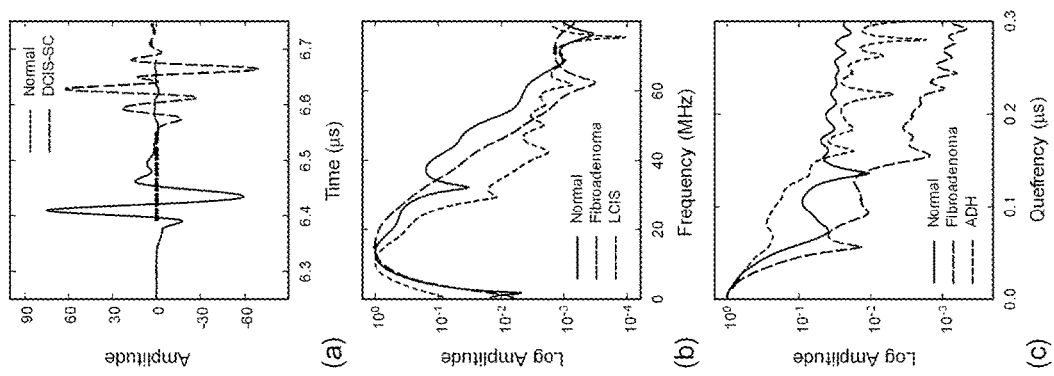
FIG. 14(a) displays examples of through-transmission waveforms of normal tissue and DCIS-SC margin specimens.
FIG. 14(b) displays examples of ultrasonic spectra from fibroadenoma, normal, and LCIS tissue specimens showing progressively increasing peak densities.
FIG. 14(c) displays modified cepstra from normal, ADH, and fibroadenoma tissue specimens showing progressively increasing cepstral slope.

The HF ultrasonic signals acquired in this study are substantially different from the typical ultrasonic signals used for medical imaging, Doppler flow imaging, or tissue characterization. Whereas typical medical ultrasound signals are comprised of scattered waves from dispersed scattering centers, typically cells or nuclei, and other tissue inhomogeneities such as blood vessel walls, the signals collected in this study were of the transmitted pulse after propagating through the tissue specimen (through-transmission mode, FIG. 2(b)) or of the specular reflection of the transmitted pulse from the surface of the second transducer (pulse-echo mode, FIG. 2(c)). Therefore, in contrast to most medical ultrasound signals, the signals in this study had pulse-like characteristics with amplitudes significantly greater than background noise. FIG. 14(a) displays examples of through-transmission waveforms of normal tissue and DCIS-SC margin specimens.

Figure 3:
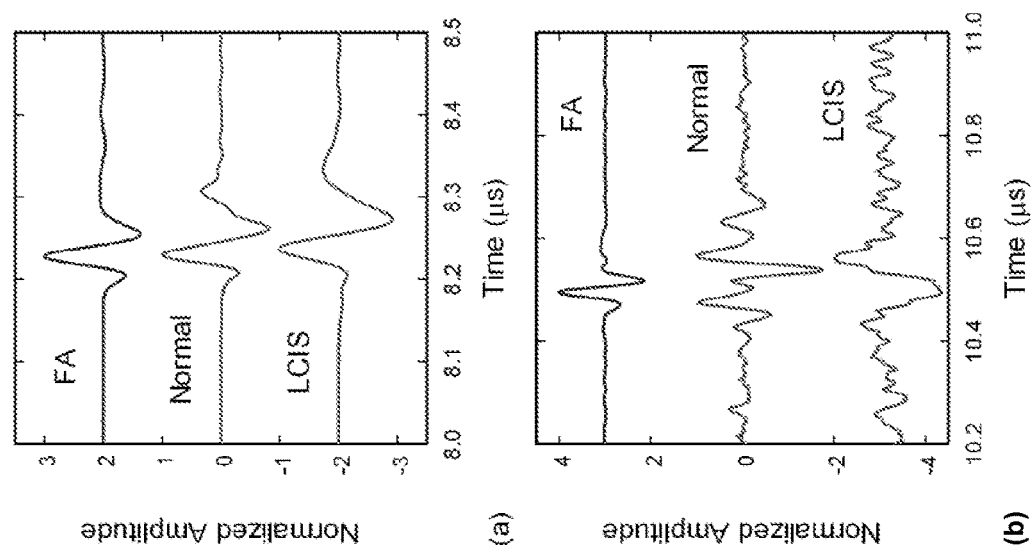
FIG. 3(a) shows ultrasonic waveforms from through-transmission measurements of surgical tissue specimens in which amplitudes have been normalized and offset for comparison.
FIG. 3(b) shows ultrasonic waveforms from pulse-echo measurements of surgical tissue specimens in which amplitudes have been normalized and offset for comparison.

For through-transmission measurements, FIG. 2(b), the ultrasonic data consisted of time-domain waveforms of ultrasonic pulses, FIG. 3(a), that were transmitted from the top transducer, passed through the specimen only once, and received by the bottom transducer. For the pulse-echo measurements, FIG. 2(c), the ultrasonic data consisted of time-domain waveforms of ultrasonic pulses, FIG. 3(b), that were transmitted from the top transducer, passed through the specimen, reflected from the surface of the bottom transducer, passed through the specimen a second time, and received by the top transducer. The ultrasonic signals for both modes of operation therefore provided a convolution of the transducer and tissue responses.

Tumor progression and other atypical conditions affect the acoustic properties of tissues by altering the cell properties, the extracellular matrix properties, and the tissue microstructure. Measurement of sound speed and attenuation can therefore be used to reveal benign, pre-cancerous, or malignant tissues in breasts. For calculation of ultrasonic sound speeds and attenuation coefficients, the arrival times and amplitudes of the time-domain waveforms were determined using a Hilbert transform. Arrival times were calibrated using a Plexiglas block as a substitute for the tissue samples. Attenuation coefficients were based on a relative scale by setting the lowest calculated attenuation value for the specimens (a fibroadenoma) to 0.003 Nepers/cm. Attenuation calculations accounted for receiver gain and specimen thickness.

Figure 4A:
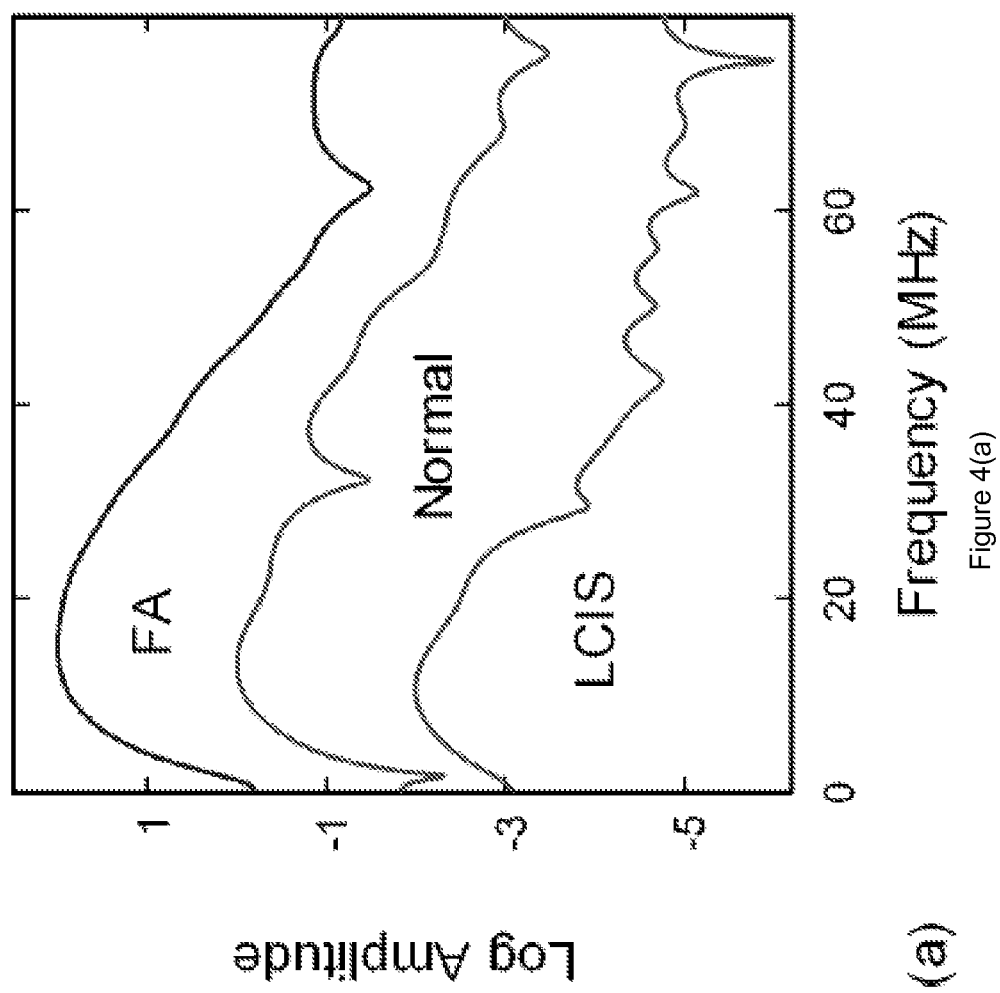
FIG. 4(a) shows ultrasonic spectra from through-transmission measurements of surgical tissue specimens in which amplitudes have been normalized and offset for comparison.
Figure 4B:
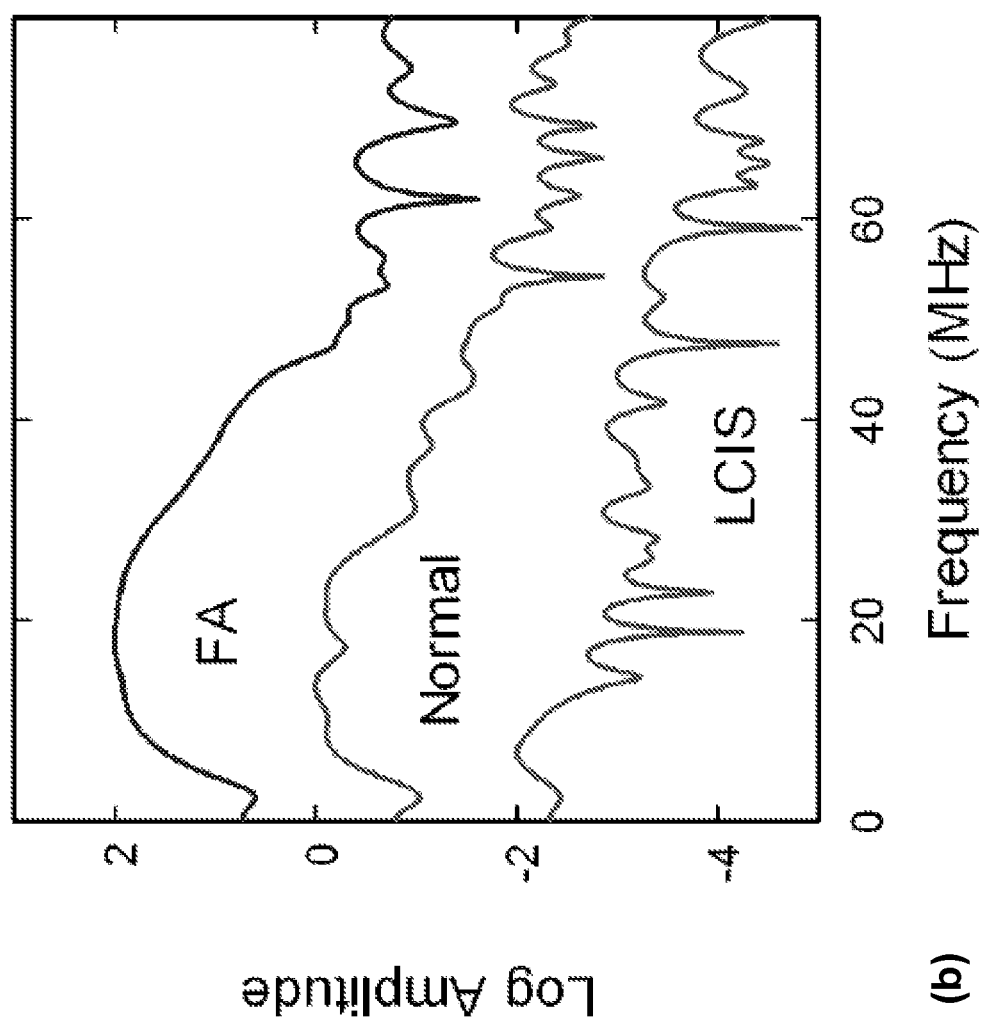
FIG. 4(b) shows ultrasonic spectra from pulse-echo measurements of surgical tissue specimens in which amplitudes have been normalized and offset for comparison.

The ultrasonic data were additionally analyzed in the frequency domain since previous numerical studies had indicated that the structure of HF ultrasonic spectra should be sensitive to neoplastic changes in breast tissues. Frequency spectra of the signals, FIGS. 4(a) and 4(b), were obtained by subtracting background waveforms from the tissue waveforms, windowing the main signals in the waveforms, padding the waveforms to 4000 points to increase the spectral resolution, and performing a fast Fourier transform (FFT). The power spectra were then derived by taking the absolute value of the complex spectra. Analysis of the spectra included correlating specific spectral features, centroid frequencies of peak clusters, and the density of peaks and valleys. The density of peaks and valleys of a spectrum, from hereon referred to as the density of peaks or peak density, was calculated by counting the number of zero crossings of the derivative of the spectrum in the 20-80 MHz band. FIG. 14(b) displays examples of ultrasonic spectra from fibroadenoma, normal, and LCIS tissue specimens showing progressively increasing peak densities.

The cepstrum is the inverse Fourier transform of the log power spectrum, and has been used to provide the mean scatterer spacing from ultrasonic data. Applications have included measuring tibial cortical thickness and the location of brachytherapy seeds in tissue. The cepstrum has also been used to obtain the mean scatterer spacing for breast tissue classified as benign, simple carcinoma, infiltrating papillary carcinoma, and fibroadenoma. However, the low spectral range, 0-10 MHz, limited the measurement of scatterer spacings to greater than 0.15 mm, and the measured mean scatterer spacing varied from 0.82±0.10 mm for normal breast tissue to 1.25±21 mm for simple carcinoma.

The cepstra of waveforms were calculated in this study by computing the spectrum from the unpadded waveform, computing the inverse FFT of the log power spectrum, and then taking the absolute value of the resulting complex function. A modified cepstrum was also used in this study to analyze data. Computation of the modified cepstrum involved using the power spectrum derived from the padded waveform, and were obtained by windowing the power spectrum from 0 to 62.5 MHz, re-padding the spectrum to 4000 points, performing a second forward FFT on the padded spectrum, taking the absolute value of the complex function, and normalizing the curves. The results produced modified cepstra that showed a maximum at 0 μs and that sloped downward with multiple peaks at various positions. The modified cepstra were analyzed by calculating the slope of the log of the modified cepstrum, which was approximately linear in the 0-0.3 μs range. The value of the modified cepstrum at 0.3 μs was also calculated. The intercept at 0.3 μs was chosen as a measurement parameter due to the change in slope of the modified cepstrum at this point in the curve. FIG. 14(c) displays modified cepstra from normal, ADH, and fibroadenoma tissue specimens showing progressively increasing cepstral slope.

The data were evaluated with bar charts using the median for the bar height and the median absolute deviation (MAD) of the analyzed parameters for the error bars. After analyzing the data by the 15 pathology types as shown in Table 1, the data were reclassified into 5 pathology types: (1) normal breast tissue, (2) FN-FA-TA (fat necrosis, fibroadenoma, and tubular adenoma), (3) benign pathologies (BC, ADH, FC, and PA), (4) ductal carcinomas (DCIS, DCIS-SC, DCIS+IDC, and IDC), and (5) lobular carcinomas (LCIS and ILC). These categories were used to assess the efficacy of the preliminary measurements in this study for differentiating carcinoma in resected margins. Specificities and sensitivities for pathology types (2)-(5) were calculated with respect to normal tissue (1). Specificities and sensitivities for the five pathology types were additionally determined using a two-parameter multivariate analysis. Finally, t-tests and one-way ANOVA tests were performed to evaluate the significance level of the results.

Sound Speed and Attenuation Measurements

The ultrasonic sound speed measurements were widely scattered and displayed large deviations, rendering a differentiation of pathology types difficult. Since the time measurements were accurate to 1 ns (through-transmission) and 2 ns (pulse-echo), the principal cause for the sound speed variations was the error in the thickness measurements, which were performed manually by measuring the displacement of the search tube that held the top transducer from the test fixture. The error in this measurement was ±0.5 mm, providing sound speed errors from 3.3% for the thickest samples (15.5 mm) to 42% for the thinnest samples (1.2 mm). Since the mean sample thickness was 5.0 mm, the average error in thickness and sound speed would be ±10%. For glandular breast tissue, this error would translate to a sound speed measurement of approximately 1.52±0.15 mm/μs. Since the ultrasonic velocities of breast fat, cysts, and tumors lie within this range (1.46, 1.57, and 1.55 mm/μs, respectively), it would be difficult to differentiate between different breast pathologies with sound speed measurements from this study.

Figure 5:
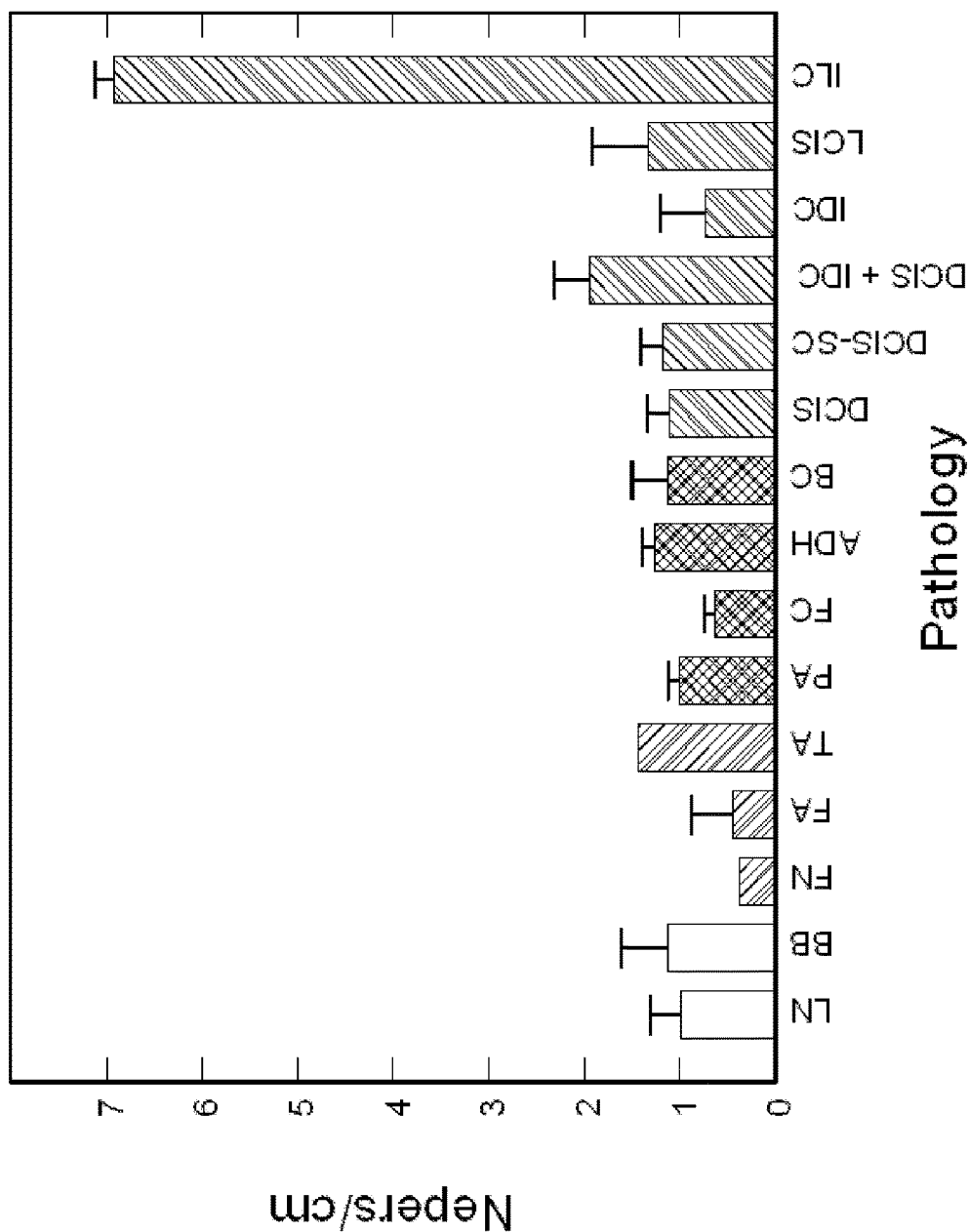
FIG. 5 shows attenuation coefficients from through-transmission data of tissue specimens, classified by pathology type.

The ultrasonic attenuation measurements were prone to similar large variations since the attenuation coefficient is inversely proportional to the thickness. FIG. 5 displays the attenuation coefficients for the through-transmission data. As shown in FIG. 5, the attenuation coefficients for most of the pathology classifications fall within the median absolute deviation range for the normal breast tissue. The exceptions are (1) fat necrosis and fibroadenoma, which fall below the median absolute deviation range for normal breast tissue, (2) DCIS+IDC, which lies immediately above the median absolute deviation range for normal breast tissue, and (3) ILC, with an attenuation substantially higher than all of the other pathologies and without overlapping deviations. These results are consistent with published data, which show lower attenuations for fat and cysts as compared to glandular breast tissue and considerably higher attenuations for tumors. The attenuation coefficients for the pulse-echo data were less accurate due to the double pass of the wave through the sample and plastic bag, giving rise to additional reflection losses.

Spectrum Analysis

Figure 6:
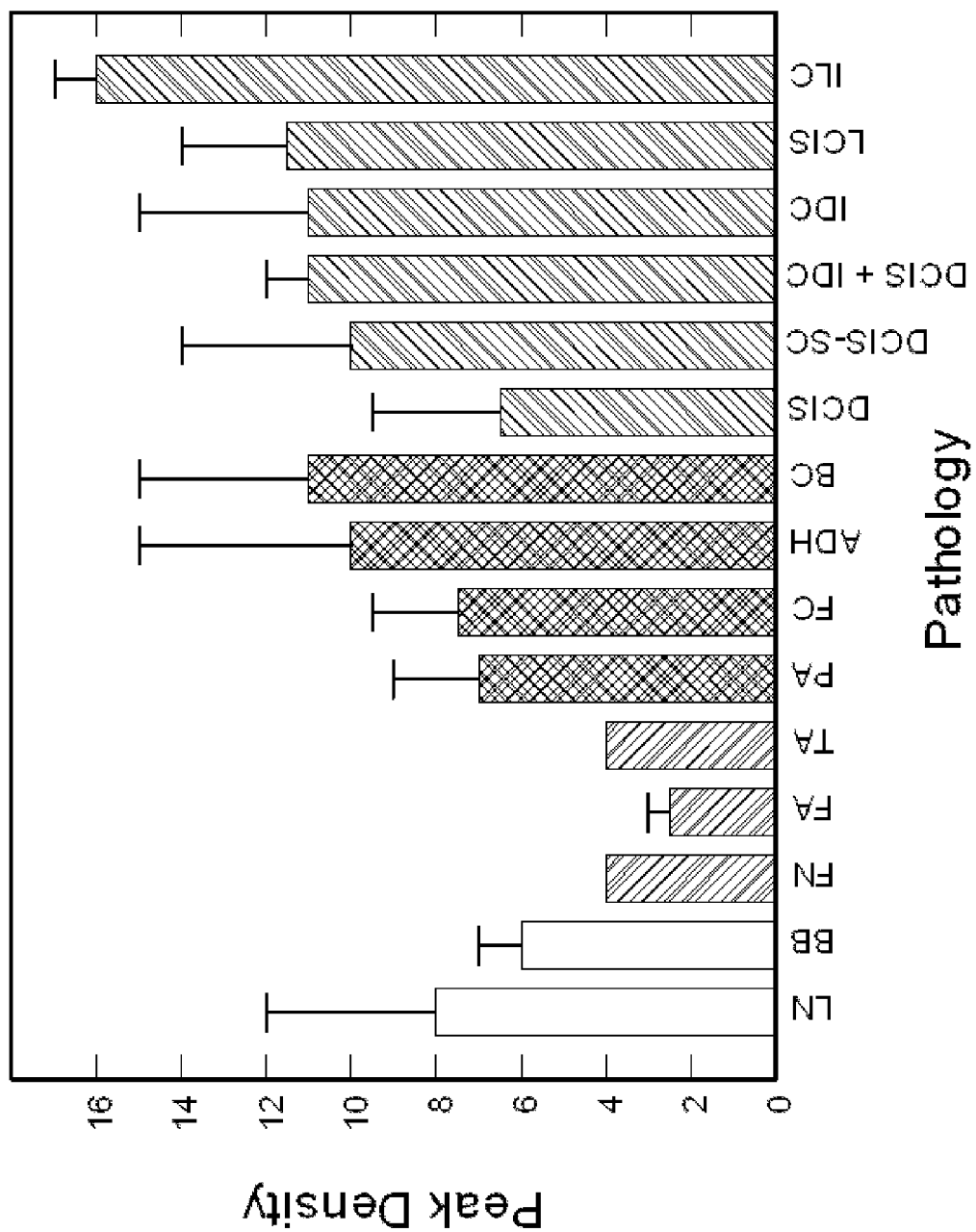
FIG. 6 shows peak densities in the 20-80 MHz band of through-transmission spectra from tissue specimens.

The ultrasonic spectra displayed a wide variation in structure that roughly corresponded to pathology. Although no single peak or group of peaks were found that could be used to differentiate tissue type, the total number of peaks and valleys in a specified spectral band appeared to be dependent on tissue pathology. FIG. 6 shows the density of peaks and valleys for the 20-80 MHz spectral band for the through-transmission data. The peak density trends indicate that a majority of the carcinoma pathologies are above the median absolute deviation range for normal breast tissue, with ILC displaying the highest peak densities. The benign breast with calcifications and ADH classifications also show significant separation from the normal breast range, whereas the fat necrosis and adenoma specimens lie below the median absolute deviation range for normal breast tissue.

Pathologies involving intraductal or intralobular changes therefore show elevated peak densities, whereas those involving stromal proliferation (adenomas) or fat necrosis show decreased peak densities. The peak densities in the 0-50 MHz band showed similar trends as the 20-80 MHz band, but with greater deviations. The peak densities from the pulse-echo data displayed less consistent trends that were less useful at distinguishing between different pathology types.

Cepstrum Analysis

A cepstrum analysis of the pulse-echo data showed that several of the samples produced multiple peaks across a range of mean scatterer spacings $d=ct/2$, where d is the spacing between scatterers, c is the tissue sound speed, and t is the time of the peak in the cepstrum. Most of the peaks occurred in an apparently random fashion and could not be correlated to pathology. However, one peak at $t=0.102$ μs ($d=77$ μm) occurred prominently in 10 of the 15 pathology types, but was absent in lymph node, fibroadenoma, tubular adenoma, DCIS+IDC, and LCIS tissues. In the 10 pathology types where the peak was present, the amplitude of the peak varied significantly from specimen to specimen, and it therefore could not be used to discriminate between the 10 pathology classifications. A secondary peak at $t=0.2$ μs was additionally present whenever the 0.102-μs peak was observed, indicating that the 0.2-μs peak was due to either a multiple wave reflection or a multiple of the mean scatterer spacing.

Figure 7:
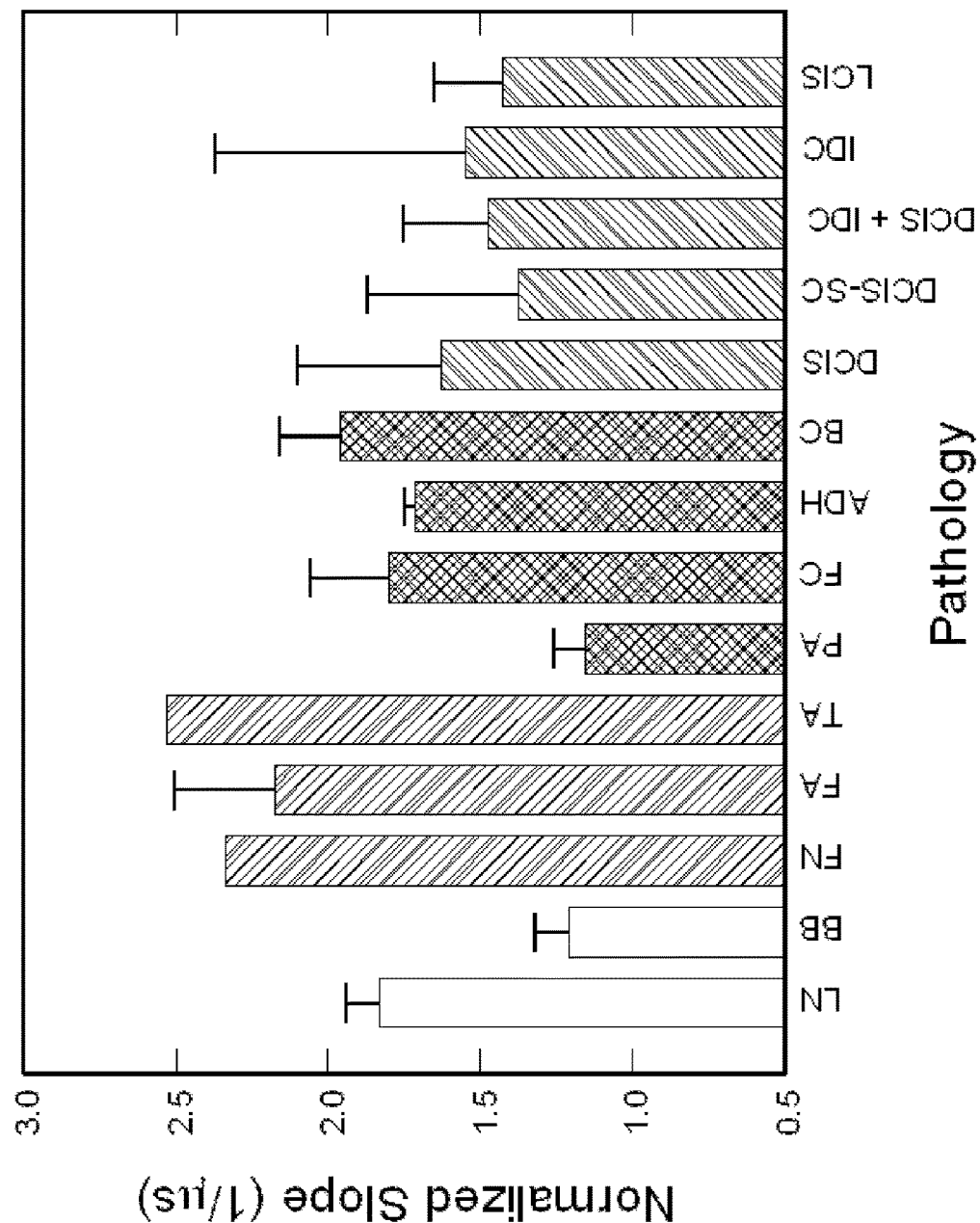
FIG. 7 shows modified cepstrum slopes from pulse-echo data of tissue specimens, classified by pathology type.

Since the slopes of the modified cepstra from 0 to 0.3 μs were negative, the absolute values of the slopes are displayed in FIG. 7 for comparison of trends. Intraductal papilloma displayed essentially the same slope and deviation values as normal breast tissue. The carcinomas displayed slopes above the median absolute deviation range for normal breast tissue, but their large deviations indicated poor separation from the normal breast tissue values. However, the other seven benign pathologies and tissues displayed significantly greater slopes than normal breast tissue, with values and deviations well above the normal breast tissue range. Fat necrosis, fibroadenoma, and tubular adenoma displayed the greatest slopes. The modified cepstrum values at 0.3 μs produced trends similar to the slopes.

Results for Re-Categorized Pathology Types

Figure 8:
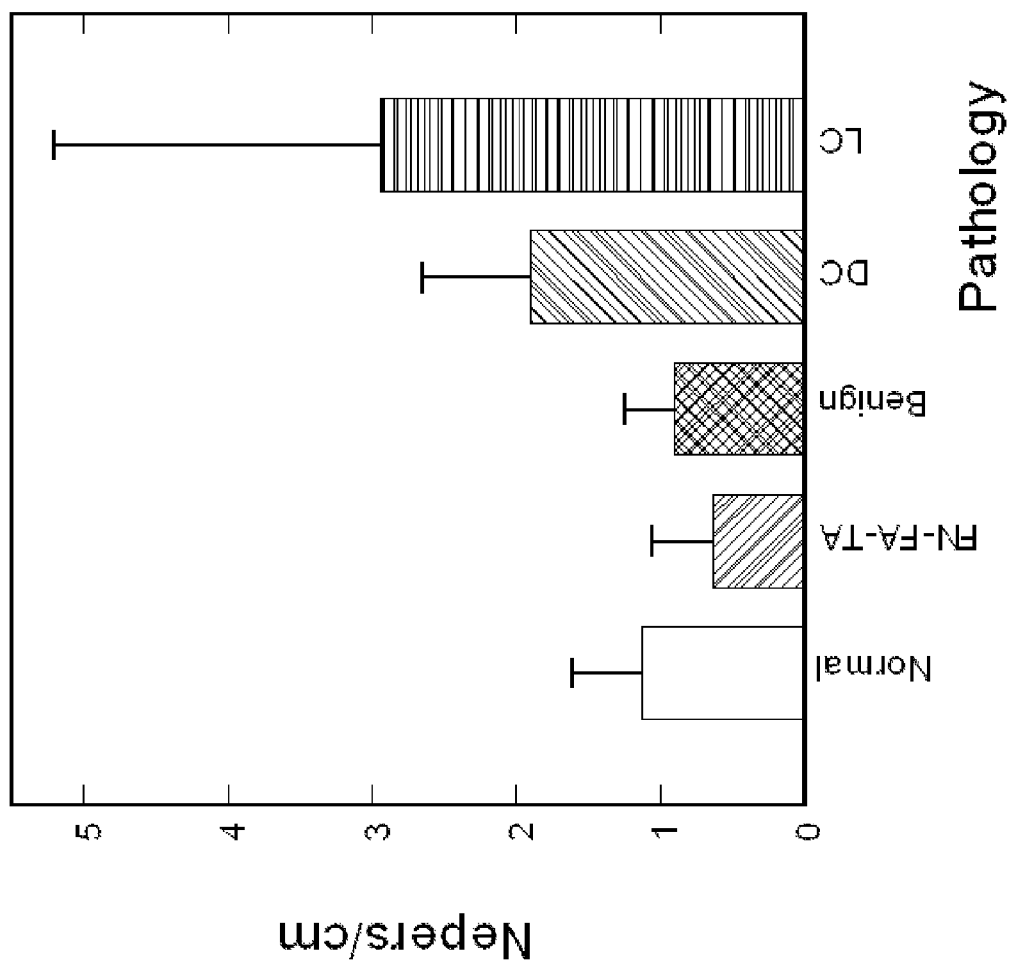
FIG. 8 shows attenuation coefficients for the reclassified tissue specimens.
Figure 9:
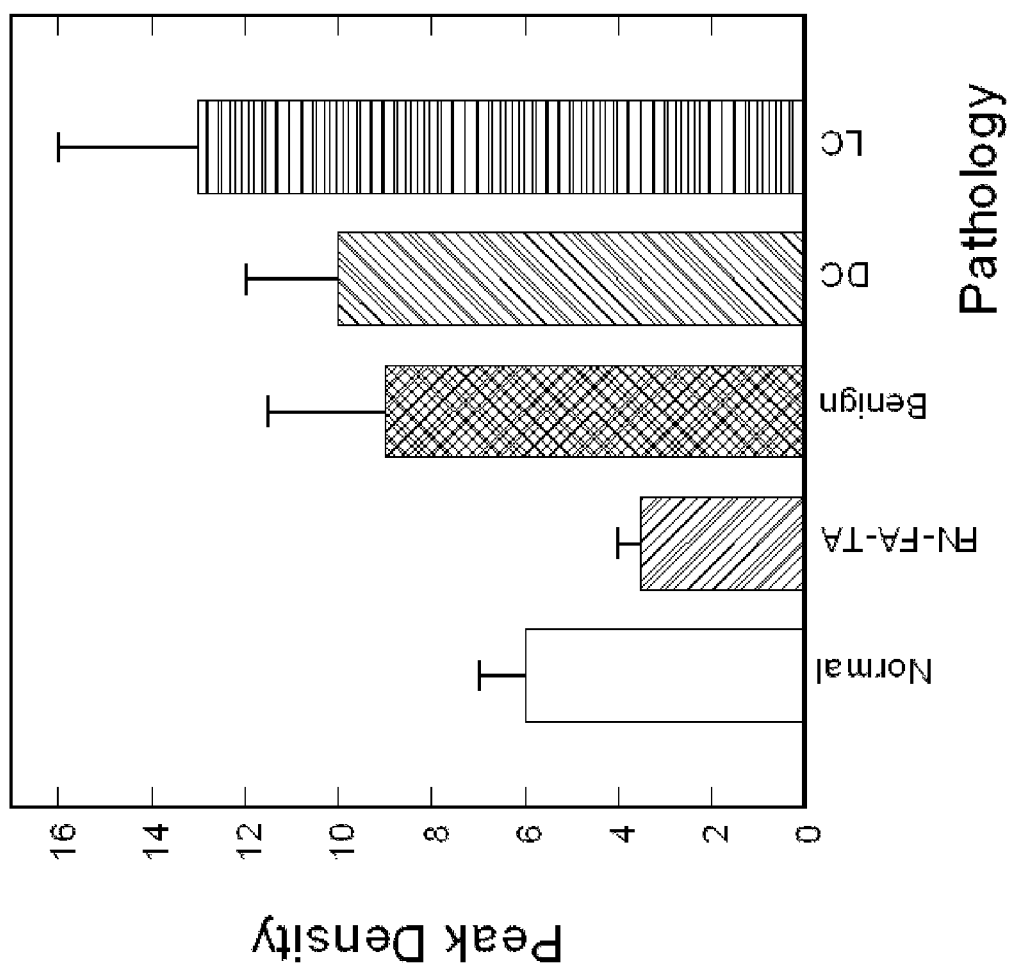
FIG. 9 shows peak densities in the 20-80 MHz band for the reclassified tissue specimens.
Figure 10:
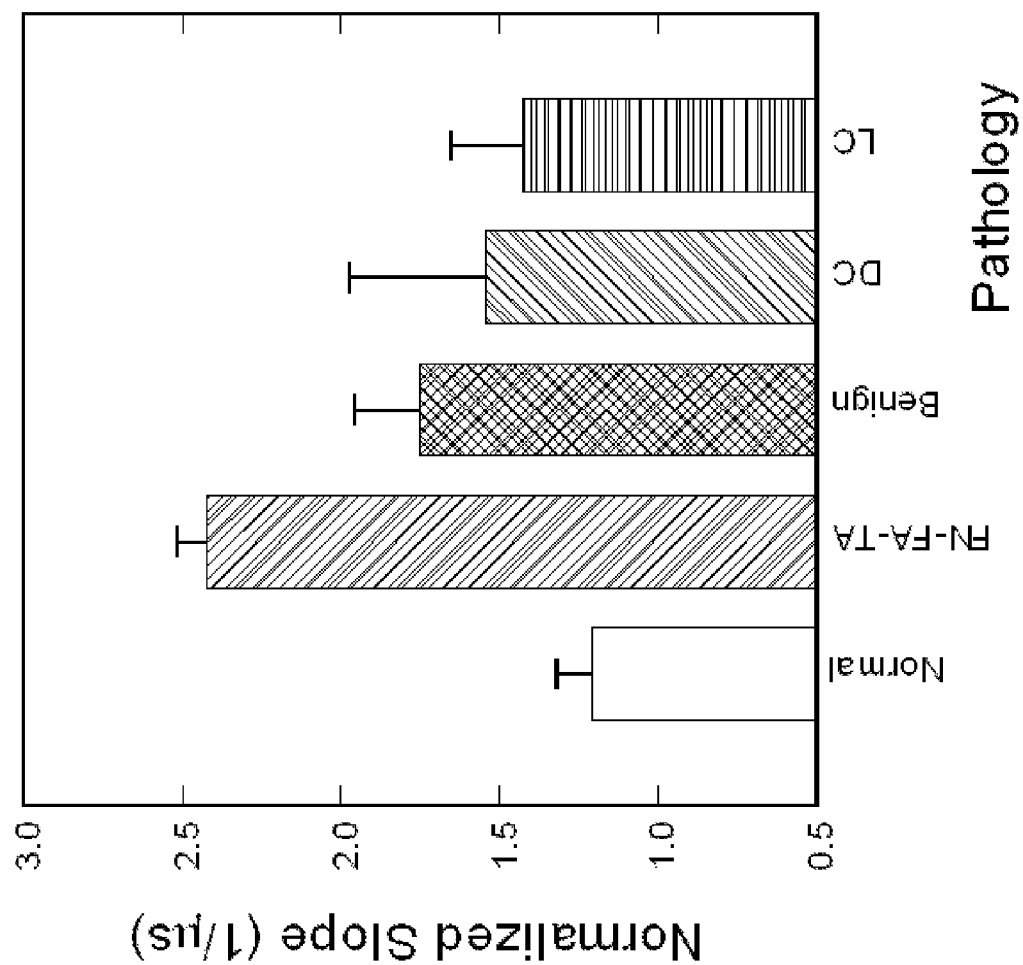
FIG. 10 shows modified cepstrum slopes for the reclassified tissue specimens.

By reclassifying the breast pathologies into five groups, the efficacy of the analysis parameters and high-frequency ultrasonic data used in this study were assessed for the detection of carcinoma in resected margins. The reclassified pathology types were (1) normal breast tissue, (2) fat necrosis/fibroadenoma/tubular adenoma (FN-FA-TA), (3) benign pathologies, (4) ductal carcinomas (DCIS and IDC), and (5) lobular carcinomas (LCIS and ILC). FIGS. 8-10 show the attenuation coefficients, peak densities, and cepstral slopes, respectively, for the reclassified pathology types.

Table 2 displays a preliminary analysis of the data shown in FIGS. 8-10 using binary classification tests to yield the specificity and sensitivity of each tissue category as compared to normal breast tissue. The specificity and sensitivity values were calculated directly from the measured data. The mean of the median values was used as the classification threshold between each tissue category and normal tissue. The peak density provided the highest values between normal and malignant tissues, whereas the cepstrum slope provided the highest values between normal tissue and benign pathologies. Both peak density and cepstrum slope gave the same values between normal and FN-FA-TA pathologies. The binary classification tests indicated higher specificities and sensitivities for lobular carcinomas than for ductal carcinomas. The specificities and sensitivities are expected to improve with more measurements from future studies.

TABLE 2

Highest specificity and sensitivity values from analysis of data classified into five pathology categories. The specificity and sensitivity for each tissue category was calculated with respect to normal breast tissue.

| Pathology | Parameter | Specificity | Sensitivity |
|---|---|---|---|
| Lobular carcinomas | Peak density | 100% | 86% |
| Ductal carcinomas | Peak density | 100% | 74% |
| FN-FA-TA | Peak density & cepstrum slope | 80% | 100% |
| Benign pathologies | Cepstrum slope | 80% | 82% |

The significance of the specificities and sensitivities in Table 2 were analyzed with t-tests. Table 3 displays the t-test and p-value for each of the four pathology groups in comparison to normal tissue, and for each of the three ultrasonic parameters. The analyses that provided statistically significant values ($p<0.05$) were peak density for lobular carcinomas, ductal carcinomas, and FN-FA-TA pathologies, and cepstrum slope for FN-FA-TA and benign pathologies. All five pathology groups were additionally analyzed with one-way ANOVA tests to determine which of the three ultrasonic parameters provided statistically significant separation of all five groups. The F-ratio for attenuation was $F_{4,31}=3.933$, indicating that the results are significant at the 5% level and very close to the 1% level of significance. Similarly, the F-ratio for peak density was $F_{4,31}=3.728$, again indicating that the results are significant at the 5% level and close to the 1% level of significance. Finally, the F-ratio for cepstrum slope was $F_{4,25}=1.854$, indicating that the results are not significant at the 10% level. Therefore, in contrast to the paired t-tests, the ANOVA tests suggest that attenuation and peak density provide the highest significance for distinguishing between the pathology types.

TABLE 3 t-test results from analysis of data classified into five pathology categories. The t-test and p-value for each tissue category was calculated with respect to normal breast tissue.

| Pathology | Attenuation | Peak density | Cepstrum slope |
|---|---|---|---|
| Lobular carcinomas | t(10) = 2.14<br>p < 0.10 | t(10) = 2.952<br>p < 0.02 | t(10) = 0.88<br>p > 0.20 |
| Ductal carcinomas | t(22) = 1.305<br>p > 0.20 | t(22) = 2.233<br>p < 0.05 | t(19) = 1.406<br>p < 0.20 |
| FN-FA-TA | t(7) = 1.278<br>p > 0.20 | t(7) = 2.609<br>p < 0.05 | t(7) = 4.615<br>p < 0.01 |
| Benign pathologies | t(21) = 1.414<br>p < 0.20 | t(21) = 1.751<br>p < 0.10 | t(20) = 2.883<br>p < 0.01 |

Multivariate Analysis

Figure 11A:
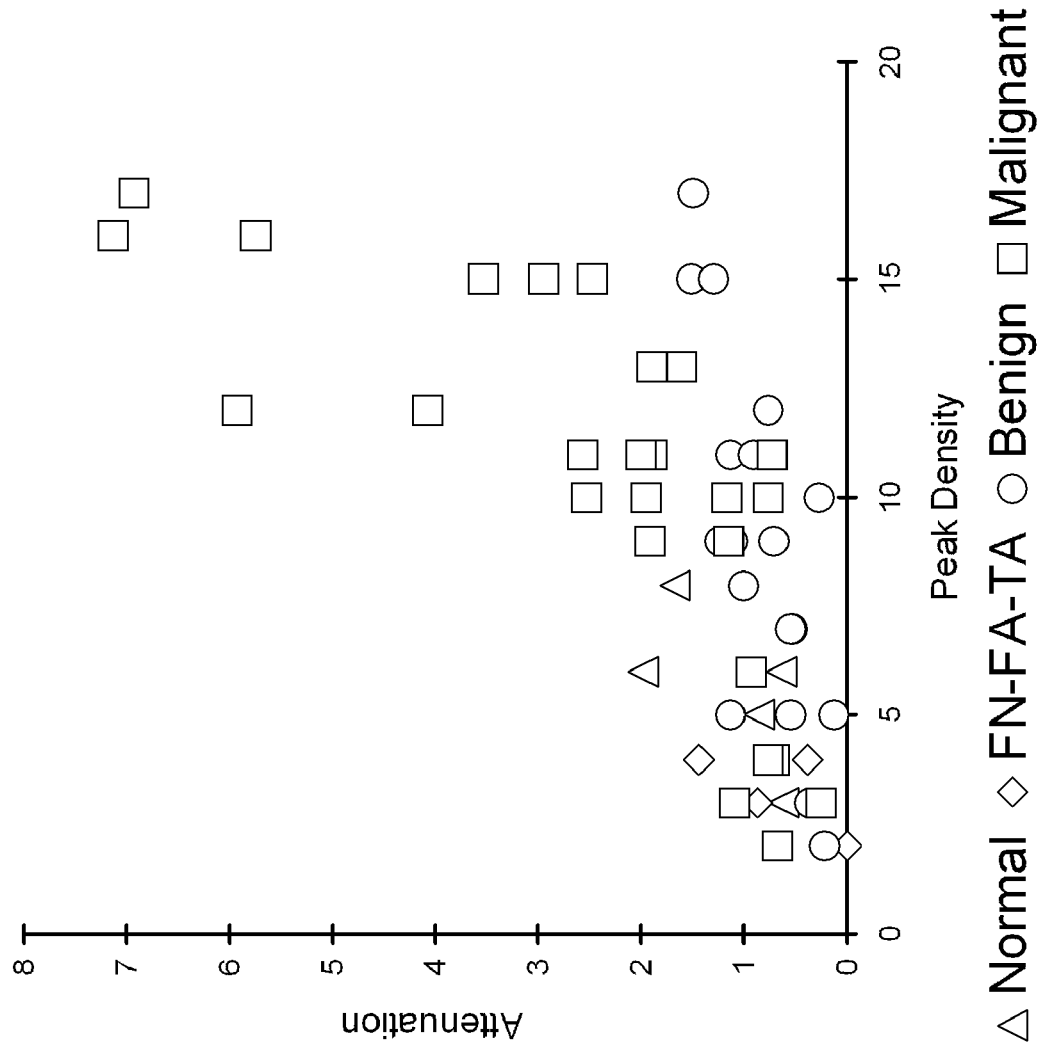
FIG. 11(a) shows multivariate analysis of peak density and attenuation parameters in ultrasonic data, in particular a non-rotated plot of attenuation vs. peak density.
Figure 11B:
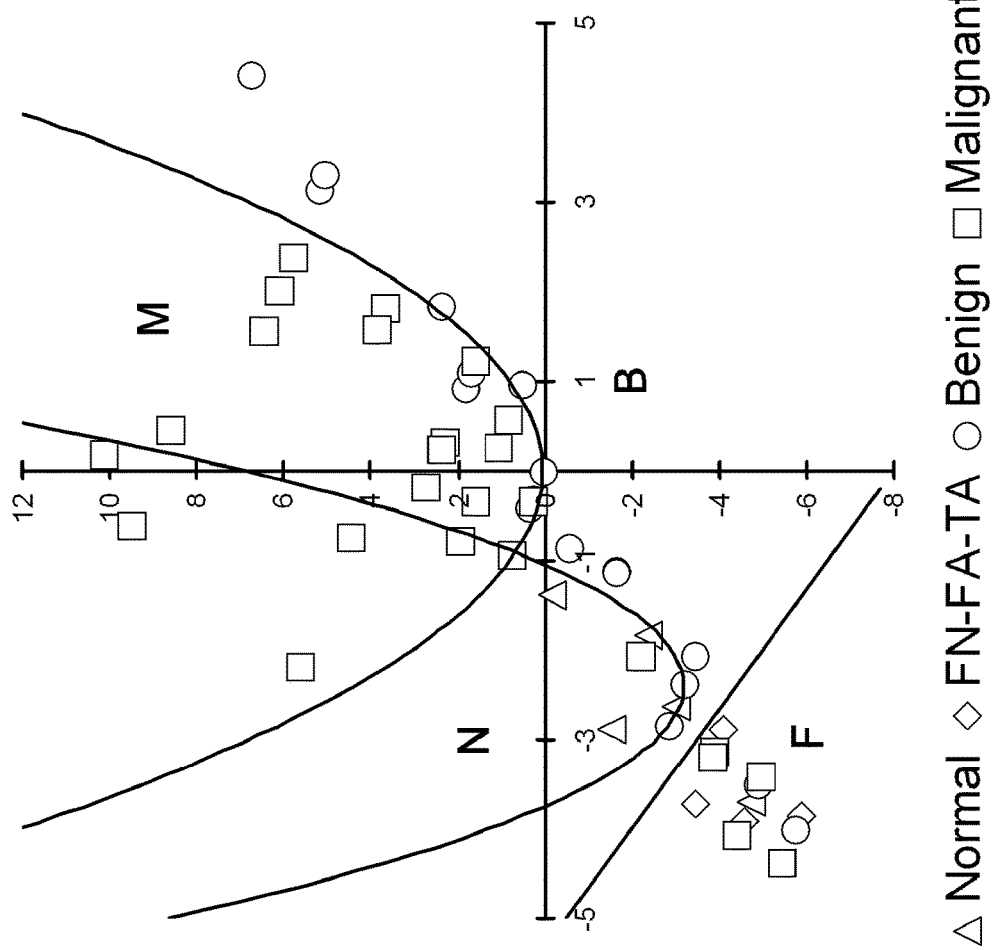
FIG. 11(b) shows multivariate analysis of peak density and attenuation parameters in ultrasonic data, in particular a rotated and translated plot of attenuation vs. peak density, showing the use of parabolic and linear curves for the classification boundaries.

A multivariate analysis was also performed on the re-categorized data by using the two-dimensional parameter space defined by attenuation and peak density (FIG. 11(a)). Classification boundaries were determined in this space by rotating and translating the coordinates of the data points and calculating linear and parabolic boundaries that maximized inclusion of a pathology category and exclusion of the other four categories (FIG. 11(b)) (in FIGS. 11(a) and 11(b): F=fat necrosis/fibroadenoma/tubular adenoma; B=benign pathology; N=normal breast tissue; M=malignant breast tissue). The one exception was for ductal and lobular carcinomas, which were intimately mixed and therefore difficult to separate in this first-look analysis. Specificities and sensitivities for each of the five pathology types, Table 4, were then calculated with respect to all of the other pathology types that were excluded by the boundary. The multivariate analysis shows that the ultrasonic measurements have good specificity and sensitivity for carcinomas with respect to all benign conditions (normal breast tissue, benign pathologies, and FN-FA-TA).

TABLE 4

Multivariate analysis results. The specificity and sensitivity for each tissue category was calculated with respect to a five-way classification system using the classification boundaries as defined in FIG. 9.

| Pathology | Specificity | Sensitivity |
|---|---|---|
| Lobular carcinomas | 85% | 86% |
| Ductal carcinomas | 85% | 74% |
| FN-FA-TA | 84% | 100% |
| Benign pathologies | 100% | 61% |
| Normal tissue | 98% | 80% |

The sensitivities for the carcinomas and FN-FA-TA pathologies remained the same in the multivariate analysis, whereas the specificities for the FN-FA-TA and benign pathologies increased. Values that decreased in the multivariate analysis included the specificities for the carcinomas and the sensitivity for the benign pathologies. Although some of the values in Table 4 are lower than those in Table 2, this is to be expected since Table 2 reports values for detecting and differentiating a particular pathology from only normal tissue, whereas Table 4 reports values for detecting and differentiating a particular pathology from all other studied pathology types. The overlap between pathology categories is therefore more evident in the multivariate analysis, and consequently the results in Table 4 are more realistic for distinguishing between pathologies such as ductal carcinoma and benign pathologies (e.g., ADH or fibrocystic changes).

The specificity and sensitivity results from this study (Tables 2 and 4) are comparable to those for various methods currently in use or under development for intraoperative margin assessments. Table 5 summarizes the reported specificity and sensitivity values for several of these methods. Since the values in Table 5 are primarily for malignant versus normal breast tissue, they are comparable most properly to the values in Table 2.

TABLE 5

Specificity and sensitivity values for various intraoperative margin assessment methods. Values represent comparison between normal vs. malignant tissue.

| Method | Specificity | Sensitivity |
|---|---|---|
| Touch preparation cytology | 83-100% | 75-96% |
| Frozen section analysis | 92-100% | 65-78% |
| Near-field RF spectroscopy | 70% | 70% |
| Raman spectroscopy | 93% | 83% |
| Optical coherence tomography | 82% | 100% |
| Fluorescence and reflectance spectroscopy | 96% | 85% |
| Low-freq. (2-10 MHz) ultrasonic attenuation | 90% | 80% |

A principal advantage of the HF ultrasonic method reported in this study over several of the methods listed in Table 5 is its ability to differentiate across a wider class of breast pathologies, including benign conditions and fat necrosis-adenomas. The ability to differentiate between different types of breast pathology, including different types of breast cancer, would be a significant advantage for an intraoperative margin assessment method. Of particular importance would be the capability to distinguish benign pathologies such as ADH and fibrocystic changes from malignancies. Although a basic multivariate analysis of our preliminary data does not yet provide high enough sensitivities and specificities (>70%) for clinically relevant detection and differentiation of all five pathology categories (specifically for benign pathologies), refinement of the measurement technique and multivariate analyses of larger, more comprehensive data sets may improve these capabilities. They may also provide further diagnostic capabilities for a more highly resolved classification system such as shown in Table 1 and FIGS. 5-7.

The strong response of HF ultrasound to lobular carcinomas (Table 2 and FIGS. 5, 6, 8, and 9) may additionally provide an accurate and clinically important method to detect ILC in surgical margins. Negative margins are difficult to achieve for ILC with conventional BCS. Six studies published between 1994 and 2006 reported 49-63% positive or close margins following the initial surgery, and a recent study reported the use of full thickness excision and oncoplastic surgery to lower the rate of positive/close margins to 39%. Taken as a pathology classification by itself, the findings of our study show that ILC is particularly easy to detect and identify as compared to other carcinomas and pathologies. Both peak density and attenuation provide specificity and sensitivity values of 100% for differentiating ILC from normal breast tissue. Attenuation also has 100% specificity and sensitivity for differentiating ILC from benign pathologies, whereas peak density has 83% specificity and 67% sensitivity.

Figure 12:
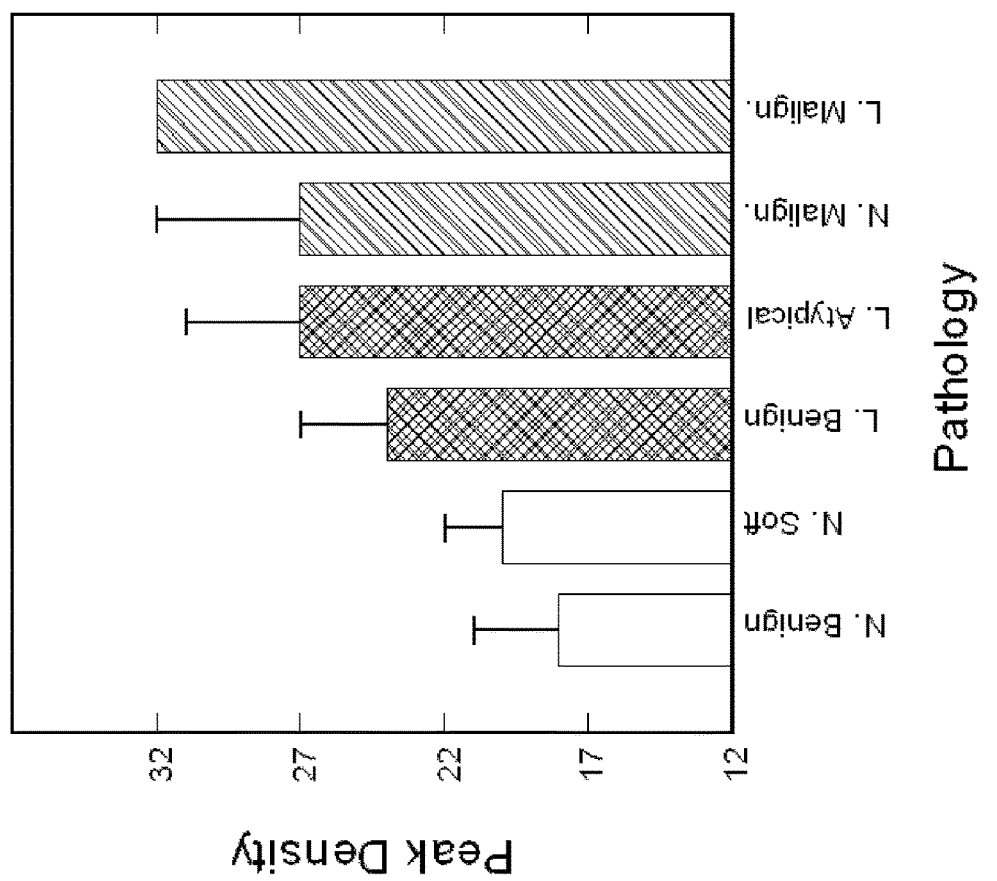
FIG. 12 shows simulated peak densities in the 20-80 MHz spectral band for a layered cylinder model, which includes arbitrarily-oriented, layered cylinders with a fluid-filled (benign or soft) or solid-filled (atypical or malignant) lumen.

In contrast to previous results from numerical models, no single peak or feature could be identified in the experimental spectra that correlated to pathology type and could therefore be used as a predictor for tissue microstructure. One parameter, however, that correlated with both benign and malignant changes to the mammary ducts was the spectral density of peaks. Pathologies that would result in enlargement of the duct or growth of a solid mass within the duct produced greater peak densities than normal breast tissue. Such pathologies included calcifications, ADH, intraductal papilloma, and DCIS solid and cribriform. These results appear to correlate strongly with the peak densities from ultrasonic backscatter spectra from a layered cylinder model, where duct enlargement or neoplasm growth in the lumen results in higher peak densities (FIG. 12). The layered cylinder model used multipole expansions to simulate ultrasonic scattering from mammary ducts represented as three-dimensional cylinders with an epithelial cell layer and interior lumen, and was similar to a model used to simulate elastic wave scattering from normal and clotted blood vessels. The observed increases in peak density with the layered cylinder model provide an interpretation of the experimental data in terms of microstructural remodeling of the normal ductal architecture. Increases in ductal diameter, wall thickness, and lumen composition (fluid, hyperplastic, or malignant) have a direct and significant affect on the peak densities.

A microstructural interpretation for the slope of the modified cepstrum is that the slope would be a measure of the distribution of scatterer spacings between 0 and 225 µm, with a large slope indicating a distribution skewed to small spacings, and a small slope indicating a distribution skewed to large spacings. The interpretation for the 0.3-µs intercept would be similar. Since the cepstra were normalized and had negative slopes, a high intercept value would indicate a shallow (small) slope and large scatterer spacings. Conversely, a low intercept value would indicate a steep (large) slope and small scatterer spacings. FIG. 7 reveals that the slopes for the modified cepstra displayed significant differences for seven of the benign pathology types as compared to the normal breast tissue and carcinoma pathologies.

At first the cepstral results appear inconsistent with a histological interpretation. Ductal dilation, thickening, and hyperplasia are characteristic of several benign pathologies including calcifications, ADH, and fibrocystic changes. These changes are expected to increase the mean spacing of the scatterers, yet the cepstral results for the ultrasonic measurements indicate that the mean scatterer spacings are less for the benign pathologies. An alternative explanation, however, is that the expansion arising from ductal dilation will decrease the interductal spacings in the tissue. This interpretation attributes the mean scatter spacing, as measured by the modified cepstrum slope and 0.3-µs intercept, to the distances between neighboring ducts. This interpretation appears consistent with the experimental data. Further simulation work with models containing multiple layered cylinders with a range of microstructures and material properties may provide a more complete correlation of the cepstrum results to ductal architecture.

The results disclosed herein indicate that high-frequency ultrasound can produce clinically relevant specificity and sensitivity values for detecting malignant tissues in surgical margins and differentiating them from normal tissue (Table 2) as well as from fat necroses, fibroadenomas, and tubular adenomas (Table 4). The sensitivity values for benign pathologies such as ADH, benign calcifications, fibrocystic change, and papilloma are relatively low (<70%), however. These values may improve with a more rigorous multivariate analysis of the parameters obtained from the ultrasonic waveform (attenuation), spectrum (peak density), and modified cepstrum (cepstral slope).

A single ultrasonic parameter is often insufficient to diagnose breast cancer in vivo, and many researchers are exploring multivariate methods to discriminate between malignant and benign pathologies in methods such as ultrasonic tomography. Sound speed and attenuation have been the two most widely used parameters to date to combine into a multivariate analysis. The results of this study, however, indicate that attenuation, spectral peak density, and modified cepstrum slope may be complementary parameters for differentiating various breast pathologies.

The peak density results (FIGS. 6 and 12) indicate that disrupted ductal architectures produce higher peak densities in selected frequency ranges as compared to normal breast tissue. Exceptions to this correlation are the fat necrosis and adenomas, which show lower peak densities than normal breast tissue and where ductal structures are either absent or severely distorted, respectively. Since both benign and malignant processes can disrupt ductal microstructures, a second parameter facilitates differentiation between these two processes. The slopes or 0.3-µs intercepts of the modified cepstra (FIG. 7) are useful in this regard in that they separate most of the benign pathologies from normal breast tissue and various carcinomas.

Numerical Modeling

The numerical models simulated 3D ultrasonic wave propagation in tissues at the microscopic level using multipole expansion methods. Multipole expansion methods are significantly more efficient than finite element, boundary element, or finite-difference time domain approaches for modeling objects with spherical or cylindrical shapes. In this study, multipole expansions were used in two different approaches to computationally model ultrasonic interactions in breast tissues at two different scales: the scale of the individual mammary duct and the scale at the cellular level.

The first approach simulated ultrasonic scattering from mammary ducts by modeling the duct as a layered cylinder. The inner core of the cylinder represented the lumen of the duct, whereas the shell of the cylinder represented the epithelial and myoepithelial cell layers. Both the stromal matrix surrounding the duct and the cell layers of the duct were given solid elastic properties. The properties of the lumen were varied from that of a fluid, representing the intraductal fluid of a normal duct, to that of a solid, representing the tumor cells of intraductal carcinoma. The 3D scattering of longitudinal and shear waves with an arbitrary angle of incidence (FIG. 15) was simulated using vector cylindrical wave functions and boundary condition solutions. The vector cylindrical wave functions were comprised of Bessel and Hankel functions for the radial components, and sine and cosine functions for the angular and axial components.

Other medical applications of cylindrical scattering models using multipole expansions have included ultrasonic scattering from bone trabeculae and clotted blood vessels. FIG. 16(a) shows a longitudinal wave incident on a normal, fluid-filled duct, FIG. 16(b), and on a malignant, solid-filled duct, FIG. 16(c). The solid-filled lumen of the malignant duct gives rise to short-wavelength shear waves within the lumen and enhances shear wave scattering in the stroma.

Figure 15:
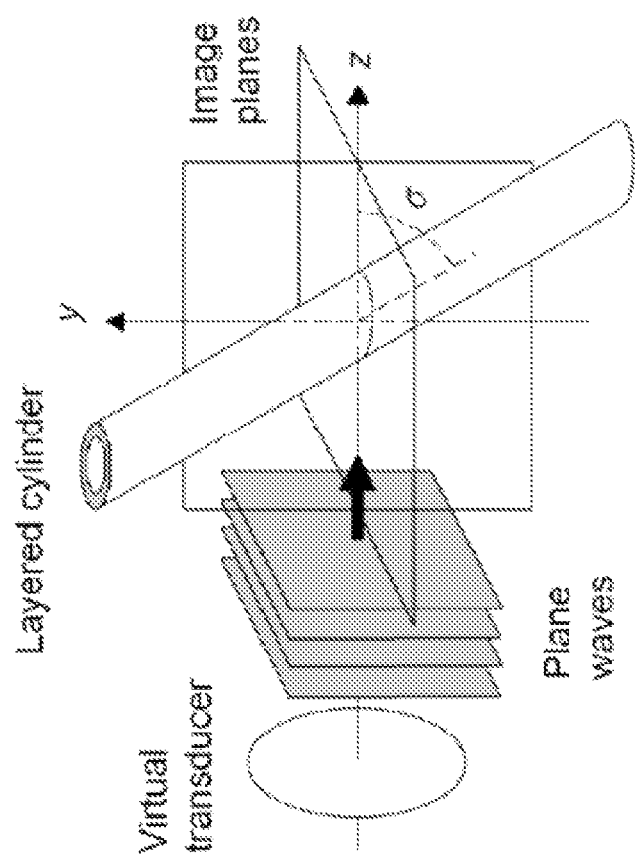
FIG. 15 shows 3D scattering of longitudinal and shear waves with an arbitrary angle of incidence simulated using vector cylindrical wave functions and boundary condition solutions.
Figure 16:
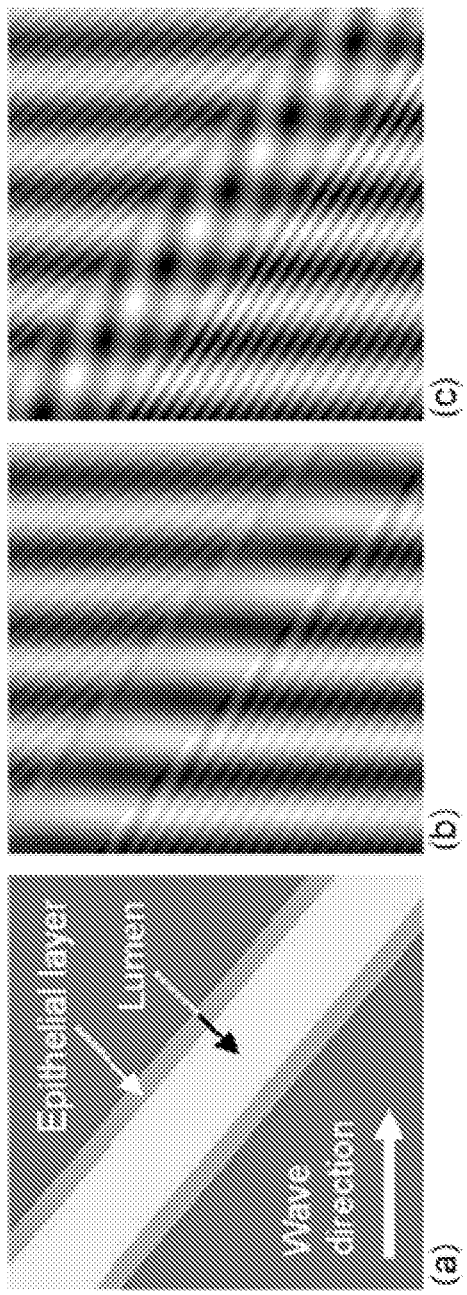
FIG. 16(a) shows a longitudinal wave incident on a normal duct.
FIG. 16(b) shows a longitudinal wave incident on a fluid-filled duct.
FIG. 16(c) shows a longitudinal wave incident on a malignant, solid-filled duct.
Figure 17:
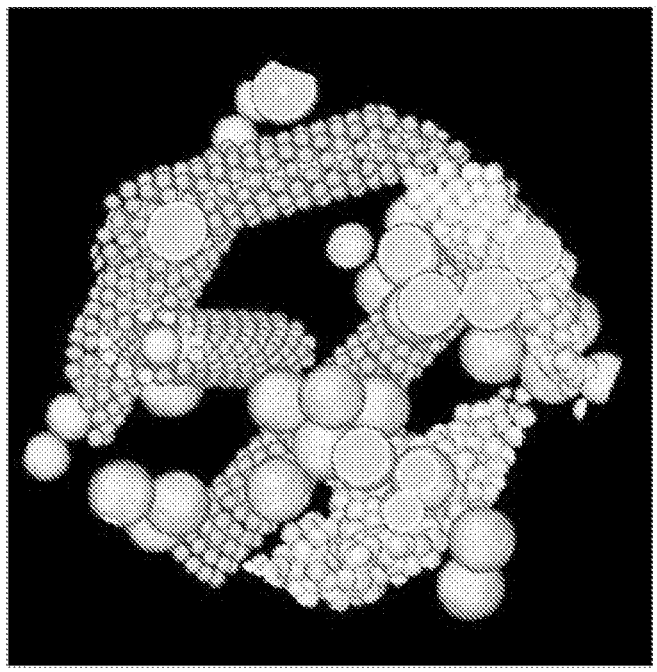
FIG. 17 shows a 3D rendering of a cell model with the cells arranged into structures representing normal ducts, malignant ducts, and clusters of adipose cells.

The second approach simulated ultrasonic scattering in breast tissue at the cellular level by modeling nucleated cells as layered spheres. The core of the sphere represented the cell nucleus, whereas the shell of the sphere represented the cell cytoplasm. The 3D scattering of longitudinal and shear waves was simulated using vector spherical wave functions and boundary condition solutions. The size and properties of the nucleus and cell were varied to model mixtures of normal epithelial, malignant epithelial, and adipose cells. A range of cell configurations containing up to 12,820 cells were modeled. Random uniform distributions of cells were simulated as well as organized cell structures representing normal, hyperplastic, and malignant ducts. FIG. 17 shows a 3D rendering of a cell model with the cells arranged into structures representing normal ducts, malignant ducts, and clusters of adipose cells. Ultrasonic spectra were calculated for mammary ducts modeled as layered cylinders (FIGS. 15 and 16). The simulated spectra were analyzed with the same methods that were applied to the experimental data in order to (1) determine a mechanistic interpretation for the ultrasonic test results and (2) validate the analysis methods. Modeled cylinders included those with normal (116 µm) or large (174 µm) outer diameters, benign (20 µm) or atypical (30 µm) epithelial-myoepithelial cell layer thickness, benign (fluid-filled) or malignant (solid-filled) lumens, and with a normal or soft shear stiffness for the stroma. Spectra were averaged over three angular orientations. Numerical considerations limited the calculations to the 20-80 MHz band.

The peak density results for the simulated spectra, FIG. 12, show that the normal-size benign ducts had the lowest number of peaks, with a progressively higher peak density for the soft stroma, large benign duct, large atypical duct, normal-sized malignant duct, and large malignant duct. The malignant ducts displayed the greatest differences from the benign ducts with a 50% higher peak density for the normal-sized ducts (normal benign vs. normal malignant) and a 78% higher peak density for the large ducts (large benign vs. large malignant).

The cepstra of the layered cylinder model spectra displayed multiple peaks that arose from the structure of the simulated individual duct. Table 6 lists the five most prominent peaks in the cepstra. Multiple peaks appear in the cepstra due to wave reflections as well as from the three different orientations of the duct with respect to the incident ultrasonic wave. Peaks that occur at least four times in the table include ones at approximately 0.106, 0.173, and 0.451 µs. Using 1.5 mm/µs as the mean sound speed in the tissue, these peaks correspond to mean scatterer spacings of 80, 130, and 340 µm. The first two spacings roughly correspond to the inner diameters of the normal size benign duct (76 µm) and large benign duct (134 µm). The third spacing is most likely a 3× multiple of the outer diameter of the normal size benign duct (3×116 µm=348 µm) and a 2× multiple of the outer diameter of the large benign duct (2×174 µm=348 µm). However, the slopes and 0.3-µs intercepts of the modified cepstra from the layered cylinder spectra did not show any trends that were significant or that could be correlated to the ultrasonic data.

TABLE 6

Peaks in the cepstra of mammary ducts modeled as layered cylinders. Normal size ducts have an ID of 76 µm and OD of 116 µm. Atypical ducts have an ID of 114 µm and OD of 174 µm. Large ducts have an ID of 134 µm and OD of 174 µm.

| Duct type | Peaks (µs) | | | | |
| --- | --- | --- | --- | --- | --- |
| Normal size, benign | 0.106 | 0.150 | 0.173 | 0.303 | 0.451 |
| Normal size, soft stroma | 0.108 | 0.149 | 0.172 | 0.303 | 0.452 |
| Large, benign | 0.109 | 0.173 | 0.224 | 0.451 | 0.677 |
| Large, atypical | 0.104 | 0.158 | 0.223 | 0.451 | 0.678 |
| Normal size, malignant | 0.124 | 0.156 | 0.187 | 0.203 | 0.238 |
| Large, malignant | 0.172 | 0.201 | 0.221 | 0.399 | 0.435 |

Twenty four spherical cell models were developed that simulated mammary duct structures and their associated neoplastic changes such as ADH and DCIS (FIG. 17). The models simulated one to seven ducts of random orientation, ducts of both circular and elliptical cross sections, ducts of a single pathology type (e.g., all ADH) or of mixed pathology types (e.g., three normal ducts and four DCIS), and ducts embedded in either a uniform stromal matrix or a matrix containing clusters of fat cells. Five to twenty simulations were ran for each model to provide a statistical sampling of ultrasonic spectra for a pathology with given parameters. The results from these models were complex, however, and difficult to interpret. Surprisingly, the simulated spectra showed little variation in structure between normal, hyperplastic, and malignant ducts. Additionally, parameters which varied in the experimental spectra, such as peak density, showed little change between different pathology types.

Figure 18:
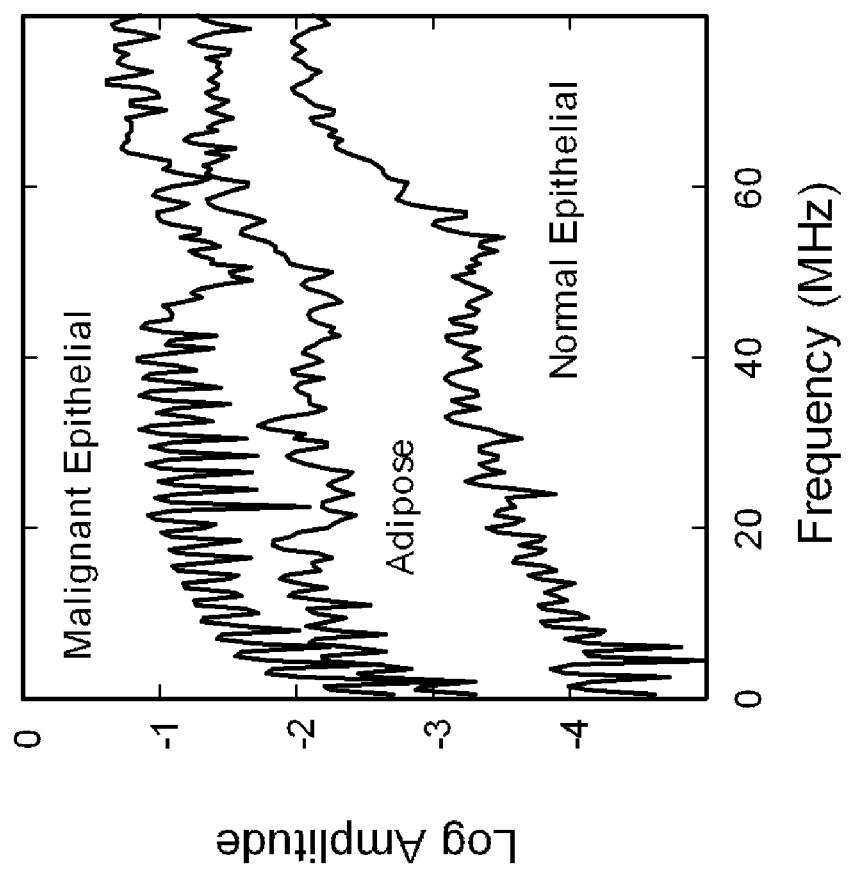
FIG. 18 shows simulated spectra based on cell models.
Figure 19:
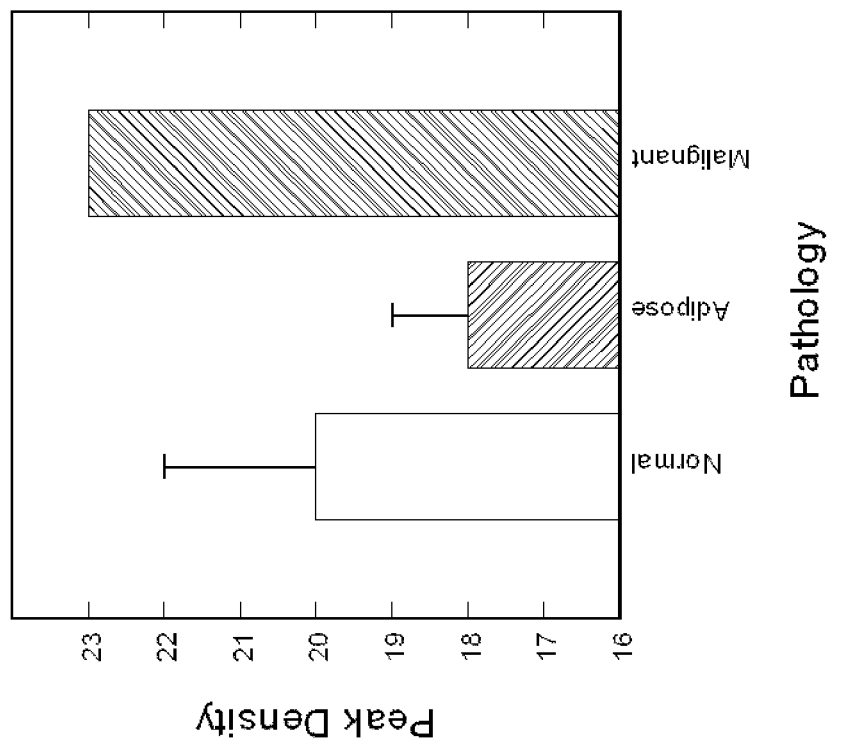
FIG. 19 shows peak densities of the spectra of FIG. 18.

Uniform distributions of cells were additionally modeled to study the effects of variations in cell structure on the simulated spectra. Previous numerical models had shown that variations in cell parameters such as nucleus size, cell size, and cell stiffness produced significant changes in the spectra. Random packings of fat cells, normal epithelial cells, and malignant epithelial cells were therefore modeled and the spectra analyzed. Cell sizes were obtained from previous studies. The simulated spectra, FIG. 18, showed marked differences between the three cell types. FIG. 19 shows the peak densities of these spectra in the 20-80 MHz range. In both this and in the 0-50 MHz band, the peak densities for the adipose cells were slightly lower than those for the normal epithelial cells, whereas the peak densities for the malignant epithelial cells were higher. The increases in peak densities for the malignant epithelial cells over the normal epithelial cells were 17% and 15% for the 0-50 MHz and 20-80 MHz ranges, respectively.

The cepstra of the uniformly distributed cell models displayed a range of peaks from 0.05 µs to 0.54 µs. The most prominent peaks appeared at 0.050 µs or the normal epithelial cells, 0.089 µs for the fat cells, and 0.070 µs for the malignant epithelial cells. These peaks correspond to mean scatterer spacings of 38, 66, and 53 µm. respectively. For comparison, the mean cell diameters were 12 µm for the normal epithelial cells, 40 µm for the fat cells, and 16 µm for the malignant epithelial cells. For the normal and malignant epithelial cells, the mean scatterer spacings are approximately 3.3× larger than the cell diameters, whereas the mean spacing for the fat cells is 1.65× larger than the cell diameter. It is therefore probable that the mean scatterer spacings for all three cell types is approximately 1.65× the cell diameters, and that the cepstrum peak for the normal and malignant epithelial cells is due to a multiple of the scatterer spacings. The mean scatterer spacing corresponds to the average nearest neighbor distance (i.e., radial distribution function), which for a non-jammed random packing of spheres is greater than the sphere diameter. Neither the slopes nor the 0.3-µs intercept values of the modified cepstra from the cell model spectra showed trends that were significant or could be correlated to the ultrasonic data.

The following references are incorporated by reference in their entirety:

1. Anscher M S, Jones P, Prosnitz L R, Blackstock W, Hebert M, Reddick R, Tucker A, Dodge R, Leight G Jr, Iglehart J D, Rosenman J: Local failure and margin status in early-stage breast carcinoma treated with conservation surgery and radiation therapy. *Annals of Surgery* 1993, 218:22-28.
2. Roukos D H, Kappas A M, Agnantis N J: Perspectives and risks of breast-conservation therapy for breast cancer. *Ann. Surg. Oncol.* 2003, 10:718-721.
3. Moore M M, Borossa G, Imbrie J Z, Fechner R E, Harvey J A, Slingluff C L Jr, Adams R B, Hanks J B: Association of infiltrating lobular carcinoma with positive surgical margins after breast-conservation therapy. *Annals of Surgery* 2000, 231:877-882.
4. Moore M M, Whitney L A, Cerilli L, Imbrie J Z, Bunch M, Simpson V B, Hanks J B: Intraoperative ultrasound is associated with clear lumpectomy margins for palpable infiltrating ductal breast cancer. *Annals of Surgery* 2001, 233:761-768.
5. Cabioglu N, Hunt K K, Sahin A A, Kuerer H M, Babiera G V, Singletary S E, Whitman G J, Ross M I, Ames F C, Feig B W, Buchholz T A, Meric-Bernstam F: Role for intraoperative margin assessment in patients undergoing breast-conserving surgery. *Ann. Surg. Oncol.* 2007, 14:1458-1471.
6. Dick A W, Sorbero M S, Ahrendt G M, Hayman J A, Gold H T, Schiffhauer L, Stark A, Griggs J J: Comparative effectiveness of ductal carcinoma in situ management and the roles of margins and surgeons. *J. Natl. Cancer Inst.* 2011, 103:92-104.
7. Shimauchi A, Yamada T, Sato A, Takase K, Usami S, Ishida T, Moriya T, Takahashi S: Comparison of MDCT and MM for evaluating the intraductal component of breast cancer. *Amer. J. Roentgenology* 2006, 187:322-329.
8. Olsha O, Shemesh S, Carmon M, Sibirsky O, Dalo R A, Rivkin L, Ashkenazi I: Resection margins in ultrasound-guided breast-conserving surgery. *Ann. Surg. Oncol.* 2011, 18:447-452.
9. Fitzgerald A J, Wallace V P, Jimenez-Linan M, Bobrow L, Pye R J, Purushotham A D, Arnone D D: Terahertz pulsed imaging of human breast tumors. *Radiology* 2006, 239:533-540.
10. Haka A S, Volynskaya Z, Gardecki J A, Nazemi J, Lyons J, Hicks D, Fitzmaurice M, Dasari R R, Crowe J P, Feld M S: In vivo margin assessment during partial mastectomy breast surgery using Raman spectroscopy. *Cancer Res.* 2006, 66:3317-3322.
11. Nguyen F, Zysk A M, Chaney E J, Kotynek J G, Oliphant U J, Bellafiore F J, Rowland K M, Johnson P A, Boppart S A: Intraoperative evaluation of breast tumor margins with optical coherence tomography. *Cancer Res.* 2009, 69:8790-8796.
12. Kennedy S, Geradts J, Bydlon T, Brown J Q, Gallagher J, Junker M, Barry W, Ramanujam N, Wilke L: Optical breast cancer margin assessment: an observational study of the effects of tissue heterogeneity on optical contrast. *Breast Cancer Research* 2010, 12:R91.
13. Lizzi F L, Greenebaum M, Feleppa E J, Elbaum M, Coleman D J: Theoretical framework for spectrum analysis in ultrasonic tissue characterization. *J. Acoust. Soc. Am.* 1983, 73:1366-1373.
14. Lizzi F L, Astor M, Feleppa E J, Shao M, Kalisz A: Statistical framework for ultrasonic spectral parameter imaging. *Ultrasound Med. Biol.* 1997, 23:1371-1382.
15. Insana M F: Modeling acoustic backscatter from kidney microstructure using an anisotropic correlation function. *J. Acoust. Soc. Am.* 1995, 97:649-655.
16. Rose J H, Kaufmann M R, Wickline S A, Hall C S, Miller J G: A proposed microscopic elastic wave theory for ultrasonic backscatter from myocardial tissue. *J. Acoust. Soc. Am.* 1995, 97:656-668.
17. Hunt J W, Worthington A E, Xuan A, Kolios M C, Czarnota G J, Sherar M D: A model based upon pseudo regular spacing of cells combined with the randomization of the nuclei can explain the significant changes in high-frequency ultrasound signals during apoptosis. *Ultrasound Med. Biol.* 2002, 28, 217-226.
18. Oelze M L, Zachary J F, O'Brien W D Jr: Characterization of tissue microstructure using ultrasonic backscatter: Theory and technique for optimization using a Gaussian form factor. *J. Acoust. Soc. Am.* 2002, 112: 1202-1211.
19. Oelze M L, O'Brien W D Jr, Zachary J F: Quantitative ultrasound assessment of breast cancer using a multiparameter approach. In 2007 *IEEE Ultrasonics Symposium:* 28-31 Oct. 2007; New York. Edited by Yuhas M P. Piscataway: IEEE; 2007:981-984.
20. Bige Y, Hanfeng Z, Rong W: Analysis of microstructural alterations of normal and pathological breast tissue in vivo using the AR cepstrum. *Ultrasonics* 2006, 44:211-215.
21. Oelze M L, O'Brien W D Jr: Application of three scattering models to characterization of solid tumors in mice. *Ultrason. Imaging* 2006, 28:83-96.
22. Oelze M L, Zachary J F: Examination of cancer in mouse models using high-frequency quantitative ultrasound. *Ultrasound Med. Biol.* 2006, 32:1639-1648.
23. Savéry D, Cloutier G: High-frequency ultrasound backscattering by blood: Analytical and semianalytical models of the erythrocyte cross section. *J. Acoust. Soc. Am.* 2007, 121:3963-3971.

24. Mamou J, Oelze, ML, O'Brien W D Jr, Zachary J F: Extended three-dimensional impedance map methods for identifying ultrasonic scattering sites. *J. Acoust. Soc. Am.* 2008, 123:1195-1208.
25. Huang S W, Li P C: Ultrasonic computed tomography reconstruction of the attenuation coefficient using a linear array. IEEE Trans. *Ultrason. Ferroelectr. Freq. Control* 2005, 52:2011-2022.
26. Li C, Duric N, Huang L: Breast imaging using transmission ultrasound: reconstructing tissue parameters of sound speed and attenuation. In 2008 International Conference on BioMedical Engineering and Informatics: 27-30May 2008; Sanya, China. Edited by Peng Y, Zhang Y. Piscataway: IEEE; 2008:708-712.
27. Jeong J W, Shin D C, Do S H, Blanco C, Klipfel N E, Holmes D R, Hovanessian-Larsen L J, Marmarelis V Z: Differentiation of cancerous lesions in excised human breast specimens using multiband attenuation profiles from ultrasonic transmission tomography. *J. Ultrasound Med.* 2008, 27:435-451.
28. Baddour R E, Sherar M D, Hunt J W, Czarnota G J, Kolios M C: High-frequency ultrasound scattering from microspheres and single cells. *J. Acoust. Soc. Am.* 2005, 117:934-943.
29. Taggart L R, Baddour R E, Giles A, Czarnota G J, Kolios M C: Ultrasonic characterization of whole cells and isolated nuclei. *Ultrasound Med. Biol.* 2007, 33:389-401.
30. Brand S, Solanki B, Foster D B, Czarnota G J, Kolios M C: Monitoring of cell death in epithelial cells using high frequency ultrasound spectroscopy. *Ultrasound Med. Biol.* 2009, 35:482-493.
31. Czarnota G J, Kolios M C, Abraham J, Portnoy M, Ottensmeyer F P, Hunt J W, Sherar M D: Ultrasound imaging of apoptosis: high-resolution non-invasive monitoring of programmed cell death in vitro, in situ, and in vivo. *Br. J. Cancer* 1999, 81:520-527.
32. Banihashemi R, Vlad R, Debeljevic B, Giles A, Kolios M C, Czarnota G J: Ultrasound imaging of apoptosis in tumor response: Novel preclinical monitoring of photodynamic therapy effects. *Cancer Res.* 2008, 68:8590-8596.
33. Vlad R M, Kolios M C, Moseley J L, Czarnota G J, Brock K K: Evaluating the extent of cell death in 3D high frequency ultrasound by registration with whole-mount tumor histopathology. *Med. Phys.* 2010, 37:4288-4297.
34. Doyle T E, Patel H, Goodrich J B, Kwon S, Ambrose B J, Pearson L H: Ultrasonic differentiation of normal versus malignant breast epithelial cells in monolayer cultures. *J. Acoust. Soc. Am.* 2010, 128:EL229-EL235.
35. Bruno I, Kumon R E, Heartwell B, Maeva E, Maev R Gr: Ex vivo breast tissue imaging and characterization using acoustic microscopy. In *Acoustical Imaging. Volume* 28. Edited by André M P. Dordrecht: Springer; 2007:279-287.
36. Doyle T E, Warnick K H, and Carruth B L: Histology-based simulations for the ultrasonic detection of microscopic cancer in vivo. *J. Acoust. Soc. Am.* 2007, 122: EL210-EL216.
37. Doyle T E, Tew A T, Warnick K H, Carruth B L: Simulation of elastic wave scattering in cells and tissues at the microscopic cancer level. *J. Acoust. Soc. Am.* 2009, 125:1751-1767.
38. Daoud M I, Lacefield J C: Stochastic modeling of normal and tumor tissue microstructure for high-frequency ultrasound imaging simulations. *IEEE Trans. Biomed. Eng.* 2009, 56:2806-2815.
39. Wear K A, Wagner R F, Insana M F, Hall T J: Application of autoregressive spectral analysis to cepstral estimation of mean scatterer spacing. *IEEE Trans. Ultrason. Ferroelectr. Freq. Control* 1993, 40:50-58.
40. Wear K A: Autocorrelation and cepstral methods for measurement of tibial cortical thickness. *IEEE Trans. Ultrason. Ferroelectr. Freq. Control* 2003, 50:655-660.
41. Mamou J, Feleppa E J: Singular spectrum analysis applied to ultrasonic detection and imaging of brachytherapy seeds. *J. Acoust. Soc. Am.* 2007, 121:1790-1801.
42. Lanfranchi M E: *Breast Ultrasound.* 2nd edition. New York: Marban Books; 2000.
43. Klimberg V S, Westbrook K C, Korourian S: Use of touch preps for diagnosis and evaluations of surgical margins in breast cancer. *Ann. Surg. Oncol.* 1998, 5:220-226.
44. Valdes E K, Boolbol S K, Cohen J M, Feldman S M: Intra-operative touch preparation cytology; does it have a role in re-excision lumpectomy? *Ann. Surg. Oncol.* 2007, 14:1045-1050.
45. Cendán J C D, Coco D, Copeland E M: Accuracy of intraoperative frozen-section analysis of breast cancer lumpectomy-bed margins. *J. Am. Coll. Surg.* 2005, 201:194-198.
46. Olson T P, Harter J, Munoz A, Mahvi D M, Breslin T: Frozen section analysis for intraoperative margin assessment during breast-conserving surgery results in low rates of re-excision and local recurrence. *Ann. Surg. Oncol.* 2007, 14:2953-2960.
47. Pappo I, Spector R, Schindel A, Morgenstern S, Sandbank J, Leider L T, Schneebaum S, Lelcuk S, Karni T: Diagnostic performance of a novel device for real-time margin assessment in lumpectomy specimens. *J. Surg. Res.* 2010, 160:277-281.
48. Haka A S, Volynskaya Z, Gardecki J A, Nazemi J, Shenk R, Wang N, Dasari R R, Fitzmaurice M, Feld M S: Diagnosing breast cancer using Raman spectroscopy: prospective analysis. *J. Biomed. Opt.* 2009, 14:054023.
49. Keller M D, Majumder S K, Kelley M C, Meszoely I M, Boulos F I, Olivares G M, Mahadevan-Jansen A: Autofluorescence and diffuse reflectance spectroscopy and spectral imaging for breast surgical margin analysis. *Lasers Surg. Med.* 2010, 42:15-23.
50. Sakr R A, Poulet B, Kaufman G J, Nos C, Clough K B: Clear margins for invasive lobular carcinoma: a surgical challenge. *Eur. J. Surg. Oncol.* 2011, 37:350-356.
51. Henni A H, Schmitt C, Cloutier G: Three-dimensional transient and harmonic shear-wave scattering by a soft cylinder for dynamic vascular elastography. *J. Acoust. Soc. Am.* 2008, 124:2394-2405.
52. Doyle T E, Factor R E, Ellefson C L, Sorensen K M, Ambrose B J, Goodrich J B, Hart V P, Jensen S C, Patel H, Neumayer L A: High-frequency ultrasound for intra-operative margin assessments in breast conservation surgery: a feasibility study. *BMC Cancer* 2011, 11:444.
53. Stotzka R, Müller T O, Ruiter N V, Schlote-Holubek K, Liu R, Göbel G, Gemmeke H: A New 3D Ultrasound Computer Tomography Demonstration System. *European Congress on Radiology* 2004.
54. Gemmeke H, Ruiter N V: 3D ultrasound computer tomography for medical imaging. *Nuclear Instruments and Methods in Physics Research Section A: Accelerators, *Spectrometers, Detectors and Associated Equipment* 2007, 580(2):1057-1065.

55. Sanpanich A, Greesuradej P, Aootaphao S, Pintavirooj C, Sangworasil M, Tosranon P: 3D Ultrasound Reflection Tomography with Matrix Linear Array Transducer. *The 3rd International Symposium on Biomedical Engineering* (ISBME 2008), p. 351-355.

Thus, the invention provides, among other things, an ultrasonic method and system for determining tissue pathology. Various features and advantages of the invention are set forth in the following claims.

What is claimed is:

1. A system for determining a pathology of a tissue sample, comprising:
    a frame including a platform configured to hold the tissue sample and height-adjustable transducer holder positioned above the platform;
    a pair of oppositely-facing ultrasonic transducers including a first ultrasonic transducer and a second ultrasonic transducer,
        wherein the first ultrasonic transducer is coupled to the frame below the platform and extends through an opening in the platform such that, when the tissue sample is held by the platform, the first ultrasonic transducer is in physical contact with the tissue sample from below,
        wherein the second ultrasonic transducer is coupled to the frame by the height-adjustable transducer and positionable such that the second ultrasonic transducer is in physical contact with the tissue sample from above; and
    a microprocessor coupled to a non-transitory computer-readable medium storing instructions, and operatively coupled to the transducers, the microprocessor configured to execute the stored instructions to
        acquire, from the pair of oppositely-facing ultrasonic transducers, a pulse-echo ultrasonic measurement and a through-transmission ultrasonic measurement of the tissue sample, wherein the tissue sample includes a margin of tissue affected by a carcinoma pathology;
        analyze, according to the instructions stored in the non-transitory computer readable medium, at least one of the pulse-echo ultrasonic measurement and the through-transmission ultrasonic measurement using time domain analysis;
        analyze, according to the instructions stored in the non-transitory computer readable medium, at least one of the through-transmission ultrasonic measurement and the pulse-echo ultrasonic measurement using frequency domain analysis by
            generating a frequency spectrum by performing a Fourier transform on at least one of the pulse-echo ultrasonic measurement and the through-transmission ultrasonic measurement,
            generating a power spectrum by taking the absolute value of the frequency spectrum,
            determining peak density in the power spectrum within a predetermined frequency range, and
            determining whether the peak density of the power spectrum within the predetermined frequency range exceeds a threshold;
        determine whether cancer is present in the margin of the tissue sample based on whether the peak density of the power spectrum within the predetermined frequency range exceeds the threshold; and
        display an indication of whether cancer is determined to be present in the margin.

2. The system of claim 1, wherein the microprocessor, in order to analyze at least one of the pulse-echo ultrasonic measurement and the through-transmission ultrasonic measurement using time domain analysis, is further configured to determine at least one of an ultrasonic sound speed and an attenuation value.

3. The system of claim 1, wherein the predetermined frequency range corresponds to a range of 20 MHz to 80 MHz.

4. The system of claim 1, wherein the tissue sample comprises breast tissue and wherein the microprocessor is further configured to classify the tissue sample as normal breast tissue, FN-FA-TA (fat necrosis-fibroadenoma-tubular adenoma), benign pathology, ductal carcinoma, or lobular carcinoma.

5. The system of claim 1, wherein the ultrasonic transducers comprise single element ultrasonic transducers.

6. The system of claim 1, wherein the ultrasonic transducers comprise ultrasonic arrays.

7. The system of claim 1, wherein the microprocessor is further configured to determine the pathology of the tissue sample based on mathematical modeling of a tissue type.

8. The system of claim 1, further comprising a pulser/receiver operatively coupled to at least one of the transducers.

9. A system for determining a pathology of a tissue sample, comprising:
    a frame including a platform configured to hold the tissue sample and height-adjustable transducer holder positioned above the platform;
    a pair of oppositely-facing ultrasonic transducers including a first ultrasonic transducer and a second ultrasonic transducer,
        wherein the first ultrasonic transducer is coupled to the frame below the platform and extends through an opening in the platform such that, when the tissue sample is held by the platform, the first ultrasonic transducer is in physical contact with the tissue sample from below,
        wherein the second ultrasonic transducer is coupled to the frame by the height-adjustable transducer and positionable such that the second ultrasonic transducer is in physical contact with the tissue sample from above; and
    a microprocessor coupled to a non-transitory computer-readable medium storing instructions, and operatively coupled to the transducers, the microprocessor configured to execute the stored instructions to
        generate, with the pair of oppositely-facing ultrasonic transducers, a tissue waveform corresponding to a pulse-echo ultrasonic measurement,
        generate, with the pair of oppositely-facing ultrasonic transducers, a background waveform corresponding to the pulse-echo ultrasonic measurement,
        generate, with the pair of oppositely-facing ultrasonic transducers, a tissue waveform corresponding to a through-transmission ultrasonic measurement of the tissue sample held by the platform, wherein the tissue sample includes a margin of tissue affected by a carcinoma pathology,
        generate, with the pair of oppositely-facing ultrasonic transducers, a background waveform corresponding to the through transmission ultrasonic measurement of the tissue sample, subtract, according to the instructions stored in the non-transitory computer readable medium, the background waveform from the tissue waveform for each of the pulse-echo ultrasonic measurement and the through-transmission ultrasonic measurement of the tissue sample, analyze, according to the instructions stored in the non-transitory computer readable medium, at least one of the pulse-echo ultrasonic measurement and the through-transmission ultrasonic measurement using time domain analysis, analyze, according to the instructions stored in the non-transitory computer readable medium, at least one of the through-transmission ultrasonic measurement and the pulse-echo ultrasonic measurement using frequency domain analysis by generating a frequency spectrum by performing a Fourier transform on at least one of the pulse-echo ultrasonic measurement and the through-transmission ultrasonic measurement, generating a power spectrum by taking the absolute value of the frequency spectrum, windowing the power spectrum, padding the windowed power spectrum, performing a forward Fourier transform on the padded and windowed power spectrum to produce a complex function, determining an absolute value of the complex function to produce a modified cepstrum, determining a slope value based on the modified cepstrum, and determining whether the slope value is within a specified range, determine whether cancer is present in the margin of the tissue sample based on whether the slope value is within the specified range, and display an indication of whether cancer is determined to be present in the margin.

10. The system of claim 9, wherein the microprocessor is further configured to analyze the modified cepstrum, the microprocessor being configured to calculate a logarithm of the modified cepstrum, and determine a slope of the logarithm of the modified cepstrum.

11. The system of claim 10, wherein the microprocessor is configured to determine a slope of the logarithm of the modified cepstrum in a range of 0 to 0.3 μs.

12. A method of treating cancer, the method comprising:

performing a first resection on a patient;

removing a tissue sample from the patient during the first resection, the tissue sample including a margin of a tissue affected by malignant cancer;

positioning the tissue sample between a pair of oppositely-facing ultrasonic transducers;

acquiring, with a microprocessor, a pulse-echo ultrasonic measurement of the tissue sample;

acquiring, with the microprocessor, a through-transmission ultrasonic measurement of the tissue sample;

generating, with the microprocessor, a frequency spectrum by performing a Fourier transform on at least one selected from a group consisting of the pulse-echo ultrasonic measurement and the through-transmission ultrasonic measurement;

generating, with the microprocessor, a power spectrum within a predetermined frequency range;

determining, with the microprocessor, peak density in the power spectrum within a predetermined frequency range;

determining, with the microprocessor, whether the peak density of the power spectrum within the predetermined frequency range exceeds a threshold; and performing a second resection on the patient in response to a determination by the microprocessor that the peak density of the power spectrum within the predetermined frequency range exceeds the threshold.

13. The method of claim 12, further comprising, determining, with the electronic processor based at least in part on the peak density, whether the margin of the tissue sample is affected by a carcinoma pathology.

* * * * *